(12) United States Patent
Vukas

(10) Patent No.: US 9,522,053 B2
(45) Date of Patent: Dec. 20, 2016

(54) DENTAL IMPLANT ASSEMBLY FOR UNIFORM DISTRIBUTION OF OCCLUSAL FORCES

(71) Applicant: Steven Vukas, Clarence, NY (US)

(72) Inventor: Steven Vukas, Clarence, NY (US)

( * ) Notice: Subject to any disclaimer, the term of this patent is extended or adjusted under 35 U.S.C. 154(b) by 36 days.

(21) Appl. No.: 14/689,383

(22) Filed: Apr. 17, 2015

(65) Prior Publication Data

US 2016/0302893 A1 Oct. 20, 2016

(51) Int. Cl.
*A61C 8/00* (2006.01)

(52) U.S. Cl.
CPC ........... *A61C 8/0086* (2013.01); *A61C 8/0012* (2013.01); *A61C 8/0022* (2013.01); *A61C 8/0054* (2013.01); *A61C 8/0068* (2013.01); *A61C 8/0074* (2013.01); *A61C 8/0089* (2013.01)

(58) Field of Classification Search
CPC ....... A61C 8/00; A61C 8/0086; A61C 8/0048; A61C 8/005; A61C 8/0068; A61C 8/0075; A61C 8/0074; A61C 8/0057; A61C 13/30; A61C 13/225; A61C 8/0028; A61C 8/009
See application file for complete search history.

(56) References Cited

U.S. PATENT DOCUMENTS

| 3,955,280 | A | * | 5/1976 | Sneer | A61C 8/0009 433/169 |
|---|---|---|---|---|---|
| 4,552,532 | A | * | 11/1985 | Mozsary | A61C 8/0086 433/173 |
| 4,881,897 | A | * | 11/1989 | Franek | A61C 8/0018 433/169 |
| 5,344,318 | A | | 9/1994 | Wilson et al. | |
| 5,425,639 | A | | 6/1995 | Anders | |
| 5,603,616 | A | | 2/1997 | Fernandes | |
| 5,873,721 | A | * | 2/1999 | Willoughby | A61C 8/0001 433/172 |
| 5,954,505 | A | | 9/1999 | Ford | |
| 2003/0129564 | A1 | * | 7/2003 | Kang | A61C 8/005 433/173 |
| 2011/0244424 | A1 | * | 10/2011 | Mehrhof | A61C 8/005 433/173 |
| 2012/0202173 | A1 | * | 8/2012 | Seo | A61C 8/0065 433/220 |

* cited by examiner

*Primary Examiner* — Cris L Rodriguez
*Assistant Examiner* — Shannel Wright
(74) *Attorney, Agent, or Firm* — Vincent G. LoTempio; Kloss, Stenger, LoTempio; David T. Stephenson

(57) ABSTRACT

A dental implant abutment assembly imitates a micro-motion mechanism to direct occlusal forces internally, and uniformly distribute the occlusal forces into the body of an ossoeintegrated dental implant. The micro-motion mechanism is configured to imitate the biomechanical behavior of the periodontal ligament through a compressive action that dampens vertical, horizontal, and angular forces. A compressive ring provides a dampening effect to supportive components of the assembly. A compressive coil redirects vertical forces along a longitudinal axis of the assembly. An implant body osseointegrates into the dental alveolus. A central mobile element seats in the dental body. The compressive coil extends along the central mobile element to absorb vertical forces. The compressive ring seats on the collar of the dental implant. A threaded cannulated housing securely holds the central mobile element and the compressive coil to form a single unit. A restorative abutment portion threadably seats on the central mobile element.

20 Claims, 19 Drawing Sheets

DENTAL IMPLANT ASSEMBLY FOR UNIFORM DISTRIBUTION OF OCCLUSAL FORCES

FIELD OF THE DISCLOSURE

The present disclosure relates generally to a dental implant abutment assembly that uniformly distributes occlusal forces during function. More so, a dental implant abutment assembly with an integrated micro-motion mechanism comprising a central mobile element, compressive coil and a compressive ring uniformly distributing occlusal forces into the body of an osseointegrated dental implant. This dental implant assembly effectively directs a greater concentration of functional forces into the body of the dental implant which resides in the cancellous alveolar bone which has more vascularity and greater pliability under function than the crestal cortical alveolar bone, where most occlusal forces on dental implants are usually concentrated. Thus, the cancellous alveolar bone, because of the aforementioned characteristics, is less prone to untoward complications from microvascular compressional bone necrosis than the cortical alveolar bone, providing a better medium to tolerate higher occlusal forces and maintain functional viability.

BACKGROUND OF THE DISCLOSURE

The following background information may present examples of specific aspects of the prior art (e.g., without limitation, approaches, facts, or common wisdom) that, while expected to be helpful to further educate the reader as to additional aspects of the prior art, is not to be construed as limiting the present disclosure, or any embodiments thereof, to anything stated or implied therein or inferred thereupon.

Typically, dental implant systems are designed to mimic the natural tooth's ability to tolerate the forces encountered during function and help to maintain the surrounding alveolar bone. However, dental implants fail to effectively mimic the shock absorbing characteristics of the periodontal ligament (PDL) for force distribution inherent in natural teeth. The goal of a dental implant system is to restore the patient to normal function, comfort, aesthetics, speech and health regardless of the current oral condition. Often, the dental implant is a surgically placed component that interfaces with the bone of the jaw or skull to support a prosthesis such as a crown, bridge, denture, facial prosthesis or to act as an orthodontic anchor.

The basis for functional stability of the dental implant is a biologic process called osseointegration where fixtures composed of materials, such as titanium, form an intimate bond to bone. The dental implant fixture is first surgically placed, so that it is likely to osseointegrate, into the surrounding alveolar bone, then a dental prosthetic is added after an appropriate time for osseointegration of the dental implant within the alveolar bone has elapsed.

One of the major factors for dental implant failure is inadequate force distribution. This phenomenon can occur with single or multiple unit implant restorations, leading to mechanical overload of the dental implants. These forces, vertical, horizontal, and angular, can cause micro motion (especially compression) of the dental implant within the alveolar bone housing which can cause microvascular injury to the supporting alveolar bone, resulting in alveolar bone degeneration from avascular necrosis and recession of viable supporting alveolar bone around the dental implant potentially resulting in implant disintegration from the alveolar housing under function as alveolar bone support on the dental implant decreases.

Because the cortical alveolar bone is more dense and rigid with less vascularity than the cancellous alvaleor bone, which is below the cortical alveolar bone, compressive functional forces are more deleterious at the cortical alveolar bone level. Higher functional forces cause microvascular damage and occlusion of vascular structures resulting in decreased blood flow and subsequent loss of viability resulting in alveolar bone recession along the alveolar bone/dental implant interface.

Typically, in the natural dentition, force distribution from occlusal forces is provided by the periodontal ligament. The periodontal ligament (PDL) is a system of biomechanically arranged fibers located between the root of a tooth, from the cementoenamel junction to root apex, and the alveolar bone housing of the tooth. The PDL allows the tooth structures to compress into the alveolar bone approximately 0.1 mm to 0.2 mm, which dissipates forces from the tooth into the alveolar bone. This compression causes a piezoelectric effect which promotes maintenance of the alveolar bone. Therefore, the PDL provides a predictable means of force distribution that allows the natural tooth to tolerate high functional loads and maintain supportive alveolar bone.

The cancellous alveolar bone has a greater pliability than the cortical alveolar bone because of the less dense biological bone composition and greater vascularity at the cancellous alveolar bone level. These aforementioned characteristics allow the cancellous alveolar bone to have tolerance for compressive forces and still maintain viability and structural support.

Other proposals have involved dental implant systems and componentry that attempt to absorb horizontal, vertical, and angular forces applied by the opposing teeth. The problem with these devices is that they do not have the benefit of compressive force dissipation inherent in a periodontal ligament. Dental implants have developing bone adhere to their mechanical threads. This osseointegration provides rigid stability to dental implants which prohibits functional compression into the alveolar bone for significant force distribution. Since osseointegration rigidity limits force distribution at the alveolar bone level, force distribution for an implant supported restoration under function is a property of the mechanically created restoration/abutment unit placed on a dental implant.

Thus, an unaddressed need exists in the industry to address the aforementioned deficiencies and inadequacies. Even though the above cited methods for a dental implant meets some of the needs of the market, a dental implant assembly that utilizes a central mobile element, a compressive coil and a compressive ring to direct occlusal forces internally and inferiorly to distribute the occlusal forces uniformly is still desired.

SUMMARY OF THE DISCLOSURE

The present disclosure is directed to a dental implant abutment assembly that utilizes a micro-motion mechanism to direct occlusal forces internally, and uniformly distribute and direct the occlusal forces inferiorly into the body of an osseointegrated dental implant which will reduce deleterious forces on the crestal cortical alveolar bone to help maintain the microvascularity and viable structural support of the alveolar bone. The micro-motion mechanism is configured to imitate the biomechanical behavior of the periodontal ligament through a compressive action that dissipates vertical, horizontal, and angular forces applied on the assembly. In essence, the assembly performs the same functional resiliency of a periodontal ligament by allowing the restoration/abutment unit to compress into the body of an osseointegrated dental implant approximately 0.1 mm to 0.2 mm, while utilizing the increased biomechanical pliability and increased microvascular stability of the cancellous alveolar bone.

This dental implant abutment assembly effectively directs a greater concentration of functional forces into the body of the dental implant which resides in the cancellous alveolar bone which has more vascularity and greater pliability under function than the crestal cortical alveolar bone, where most occlusal forces on dental implants are usually concentrated. Thus, the cancellous alveolar bone, because of the aforementioned characteristics, is less prone to microvascular compressional bone necrosis than the cortical alveolar bone, a better medium to tolerate higher occlusal forces and maintain functional viability.

The assembly utilizes a central mobile element, a compressive coil and a compressive ring to absorb and redirect the occlusal forces produced under function. The central mobile element, compressive coil and the compressive ring make up a substantial portion of the load dispersion components for the assembly. The central mobile element, compressive coil and the compressive ring enable the assembly to provide about 0.1 mm to 0.2 mm of compressive force distribution into the body of and osseointegrated dental implant. The compressive ring provides a dampening effect to key supportive components of the assembly. The central mobile element and compressive coil direct and dissipate functional forces along a longitudinal axis of the assembly.

The assembly comprises a central mobile element that forms a vertical support for the compressive ring and the coil. The central mobile element supports the compressive ring on a shoulder portion that broadens laterally from the longitudinal axis of the central mobile element to provide a supportive surface. The central mobile element functions with the attached compressive coil along the longitudinal axis. The compressive coil has a diameter that forms a intimate fit along the inferior portion of the central mobile element. An abutment attaches on to the superior threaded portion of the central mobile element, creating a compressive force on the compressive ring situated on the inferior aspect of the restorative abutment portion and the external locking surface of the threaded cannulated housing. The shoulder and the inferior portion of the central mobile element with attached compressive coil is encased in a hollow chamber of the threaded cannulated housing which resides within the body of the dental implant. The implant body receives functional forces directed by the entire abutment unit formed by the central mobile element, the compressive ring, the compressive coil, and the restorative abutment portion. Finally, a dental prosthesis screws onto the restorative platform of the collar of the dental implant.

The assembly comprises a dental implant, which is comprised of a body and a collar that forms an anchor for the assembly through osseointegration with the alveolar bone. The implant body is defined by an external threaded surface and an internal threaded bore. The external threaded surface is disposed to reside substantially in the pliable cancellous alveolar bone. The dental implant collar, which resides in the rigid cortical alveolar bone, forms a restorative platform for supporting a dental prosthesis and a compressive ring. The external threaded surface of the dental implant threadably mounts into the native alveolar bone to form an anchor for the assembly. The external threaded surface provides surface area for developing bone to form and adhere to the external mechanical threads of the dental implant. This osseointegration helps create a rigid stability to the assembly, which limits significantly compression of the dental implant into the alveolar bone. This rigid integration limits the distribution of functional forces into the alveolar bone. The internal threaded bore of the dental implant extends along a longitudinal axis of the assembly and terminates at a bore base. In most current implant systems, occlusal forces are prosthetically directed by rigid connection of componentry into the internal threaded bore with the highest concentration of functional forces located at the interface of the prosthesis, implant collar, and crestal alveolar bone, which is highly prone to compressive microvascular degeneration.

The dental abutment assembly further comprises a central mobile element that is disposed to extend through the internal threaded bore of the implant body. The central mobile element is generally cylindrical and has a tapered shape. The central mobile element is defined by a threaded narrow superior portion, a tapered shoulder portion, and a broadened inferior portion. The threaded superior portion is generally narrower than the inferior portion. The tapered shoulder portion aligns with the inferior aspect of the collar of the dental implant. The inferior portion of the central mobile element rests about 1 millimeter above the bore base of the internal threaded bore. This bore gap enables a slight vertical displacement of the central mobile element within the threaded bore under function, which helps dissipate occlusal forces.

A compressive coil is configured to wrap around the tapered shoulder and inferior portion of the central mobile element. The compressive coil is defined by a coil base and a coil apex. The coil extends approximately between the shoulder portion of the central mobile element at the compressive coil base, and the inferior portion of the central mobile element at the compressive coil apex. The compressive coil is one of the components that helps dampen the occlusal forces on the assembly. The compressive coil is configured to compress about 0.1 to 0.2 millimeters in the loaded position, and then return to a natural extended position in the unloaded position. Specifically, the compressive coil at least partially supports vertical displacement of the central mobile element for uniformly distributing functional forces into the body of the dental implant.

The dental implant abutment assembly further includes a threaded cannulated housing that is configured to securely retain the central mobile element and the attached compressive coil, while also firmly mounting within the dental implant body. The threaded cannulated housing comprises a hollow inner housing chamber. The hollow inner housing chamber is configured to enable passage of the central mobile element and the attached compressive coil. The hollow chamber and the inner housing channel of the threaded cannulated housing is tapered superiorly. This tapered configuration is arranged to restrict movement of the central mobile element and the compressive coil in the hollow inner housing channel. The threaded cannulated housing also comprises an outer housing threaded surface. The outer housing threaded surface is disposed to threadably engage the internal threaded bore of the dental implant body via mechanically applied torque.

In some embodiments, the threaded cannulated housing also comprises a terminal end and a locking end. The locking end includes an inner ridge and an external locking surface. The external locking surface may have three depressions that enable a torque tool to rotatably engage the threaded cannulated housing with the internal threaded bore of the dental implant body. A 1 mm functional space forms between the threaded superior portion of the central mobile element and the external locking surface of the housing. The inner ridge of the locking end engages the inferior shoulder portion of the dental implant and the threaded superior portion of the threaded internal bore of the dental implant.

In some embodiments, the dental implant abutment assembly comprises a compressive ring that helps dampen occlusal forces on the assembly and the dental implants restorative platform. The compressive ring is defined by a central hole and a resilient composition. The threaded superior portion of the central mobile element passes through the central hole of the compressive ring. The compressive ring substantially occupies the functional space formed between the junction of the inferior aspect of the restorative abutment portion and the threaded superior portion of the central mobile element superiorly and the external locking surface of the threaded cannulated housing inferiorly. The compressive ring is configured to compress about 0.1 mm. The compressive ring also helps restrict moisture contamination in the functional space between the junction of the inferior aspect of the restorative abutment portion and the threaded superior portion of the central mobile element superiorly and the external locking surface of the threaded cannulated housing inferiorly.

The assembly further includes a restorative abutment portion that is configured to attach the central mobile element and to a dental prosthesis. Depending on the presenting occlusal scheme and on the final restoration to be attached to the restorative abutment, the restorative abutment may have the same dimensions superiorly and inferiorly, be wider at the base, tapering to a narrower superior dimension, or custom-made to provide optimal force distribution. The restorative abutment portion is defined by an inferior aspect having a wider central threaded portion and a superior aspect having a narrower central threaded portion. The inferior aspect of the restorative abutment portion is disposed to engage the compressive ring positioned on the collar of the dental implant. The compressive ring helps dampen occlusal forces on the abutment and restorative platform of the dental implant. The wide central threaded area of the inferior aspect of the restorative abutment portion is disposed to threadably engage the threaded superior portion of the central mobile element for compressing the force distribution abutment assembly onto the compressive ring and activating the compressive coil within the body of the dental implant. The narrow central threaded area of the superior portion of the restorative abutment provides the means by which to attach and retrieve the functional prosthesis via a retention screw to the assembly. The prosthesis biomechanical composition (s) (i.e. porcelain titanium noble metals etc.) have inherent physical properties (modulus of elasticity, compressive strength, malleability, etc. and the like) which transmit functional forces applied from opposing structures by compression and flexure of the materials along the abutment assembly and against the rigid restorative platform collar initiating the function of the entire assembly and its componentry.

Those skilled in the art will recognize that uniform increased force distribution at the abutment level of the assembly provides a means for increasing overall functional force distribution. This particular type of force distribution may allow the assembly to function and maintain its viability when increased functional forces are applied. The compressive ring and the compressive coil enable the assembly to have a compressive force dissipation capability similar to that allowed by the periodontal ligament, which provides greater success for restorations that may combine dental implants and natural teeth as abutments within the same restoration.

Additionally this particular type of force distribution would be beneficial in situations where anatomical constraints exist, such as the maxillary sinus or inferior alveolar nerve, which dictates the placement of shorter dental implants, possibly causing a less than ideal restoration to implant ratio whereby crown length approaches implant length. Ideally the dental implant should be about 1.5 to 2 times greater in length than the restoration mimicking the ideal crown to root ratio of natural teeth. It is a general objective to provide a dental implant abutment assembly for uniform distribution of occlusal forces that imitate a micromotion mechanism for directing occlusal forces internally, and uniformly distributing the occlusal forces into the body of the dental implant.

It is another objective to provide a dental implant abutment assembly for uniform distribution of occlusal forces to utilize the increased pliability and bone sustaining increased microvascularity of the cancellous alveolar bone.

It is another objective to provide a dental implant abutment assembly for uniform distribution of occlusal forces to perform the same task of a periodontal ligament by allowing a prosthesis/abutment unit to compress into the body of a dental implant approximately 0.1 mm to 0.2 mm.

It is another objective to provide a dental implant abutment assembly for uniform distribution of occlusal forces with a compressive ring and a compressive coil internally in the dental implant force distribution abutment assembly that dampens the encountered occlusal forces.

Another objective is to provide a dental implant abutment assembly for uniform distribution of occlusal forces configured to threadably assemble and disassemble the dental implant assembly through a screw and a torque tool.

Yet another objective is to provide a dental implant abutment assembly for uniform distribution of occlusal forces with a compressive ring that compresses between 0.1 mm to 0.2 mm, and also inhibits moisture contamination of the force distribution abutment components.

Still another objective is to provide a dental implant abutment assembly for uniform distribution of occlusal forces with a compressive coil that extends along the inferior length of the central mobile element to absorb and direct functional forces on the force distribution abutment assembly into the body of the dental implant.

Still a further objective is to provide a dental implant abutment assembly for uniform distribution of occlusal forces with a threaded cannulated housing 136 that is rotatably adjusted.

Another objective is to provide a dental implant abutment assembly for uniform distribution of occlusal forces with an interchangeable dental prosthesis that threadably attaches to the restorative abutment portion of the force distribution abutment and the restorative platform of the collar of the dental implant.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The present disclosure and the manner in which it may be practiced is further illustrated with reference to the accompanying drawings wherein.

Like reference numerals refer to like parts throughout the various views of the drawings.

DETAILED DESCRIPTION OF THE DISCLOSURE

Figure 1A:
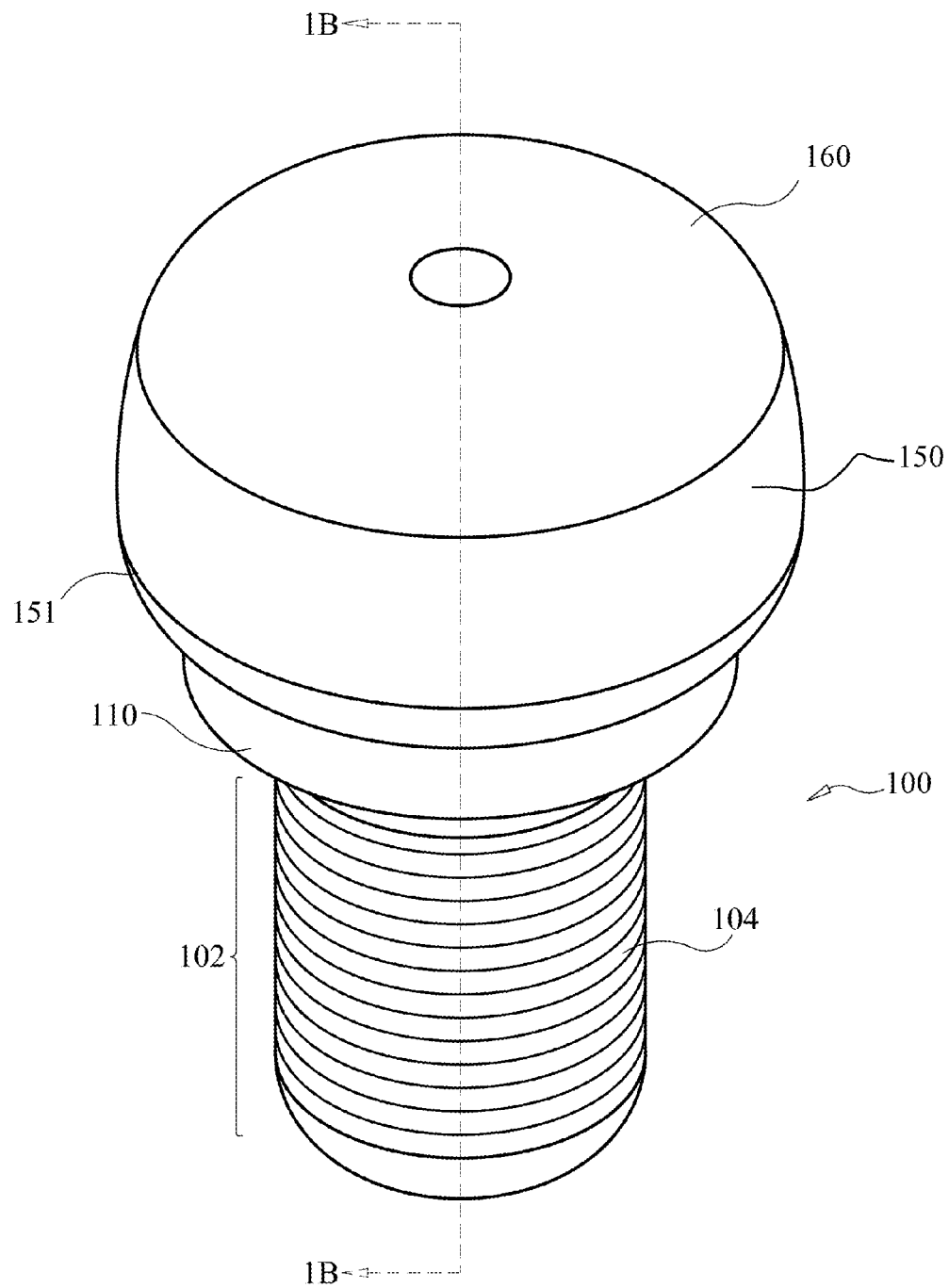
FIG. 1A illustrates top perspective view of the dental implant abutment assembly for uniform distribution of occlusal forces of the present disclosure.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," "cross-sectional," "sectional" and derivatives thereof shall relate to the disclosure as oriented in FIG. 1A. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this disclosure as required by 35 U.S.C. §112.

In one embodiment of the present disclosure, presented in FIGS. 1A-18, a dental implant abutment assembly 100 ("the assembly") imitates a micro-motion mechanism to direct occlusal forces internally, and uniformly distribute the occlusal forces into the body of an osseointegrated dental implant. The micro-motion mechanism is configured to imitate the biomechanical behavior of the periodontal ligament through a compressive action that dissipates vertical, horizontal, and angular forces applied on the assembly. In essence, the assembly 100 mimics the same resiliency properties of a periodontal ligament by allowing the prosthesis/force distribution abutment unit to compress into the body of an osseointegrated dental implant in the range of approximately 0.1 mm to 0.2 mm.

In some embodiments, the dental implant abutment assembly 100 may imitate a micro-motion mechanism to direct occlusal forces internally, and uniformly distribute the occlusal forces into the body of an osseointegrated dental implant. In this manner, the assembly 100 is similar to a micro-motion mechanism in that it imitates the biomechanical behavior of the periodontal ligament through a compressive action that absorbs and dampens vertical, horizontal, and angular forces applied onto the assembly 100 from a loaded position 164 (see FIG. 9B, and then relaxes into an unloaded position 162 (see FIG. 9A). This micro-motion action centrally concentrates occlusal forces and directs those forces inferiorly taking advantage of force distribution into the body of the dental implant. Because of the force distribution more inferiorly into the body of the dental implant, the increased pliability and microvascular stability of the cancellous alveolar bone is better able to tolerate functional forces than the less vascular cortical alveolar bone at the restoration/implant collar interface.

Those skilled in the art, will recognize that this allowable compression is generally not possible with standardized dental implants. However, the dental implant abutment assembly 100 helps dissipate occlusal forces from the prosthesis/force distribution abutment unit into the body of an osseointegrated dental implant, and also on the assembly 100. In one embodiment, the assembly 100 is effective for uniformly distributing a functional load into the body of an osseointegrated dental implant thereby reducing higher functional stresses on the cortical alveolar bone to increase its viability. In light of the present teachings, those of ordinary skill in the art will recognize that the assembly 100 directs a greater concentration of functional forces into the body of a dental implant which resides in the cancellous alveolar bone which has more vascularity and greater pliability under function than the crestal cortical alveolar bone, where most occlusal forces on dental implants are usually concentrated. Thus, the cancellous alveolar bone, because of the aforementioned characteristics, is less prone to microvascular compressional bone necrosis than the cortical alveolar bone, a better medium to tolerate higher occlusal forces and maintain functional viability.

Figure 4A:
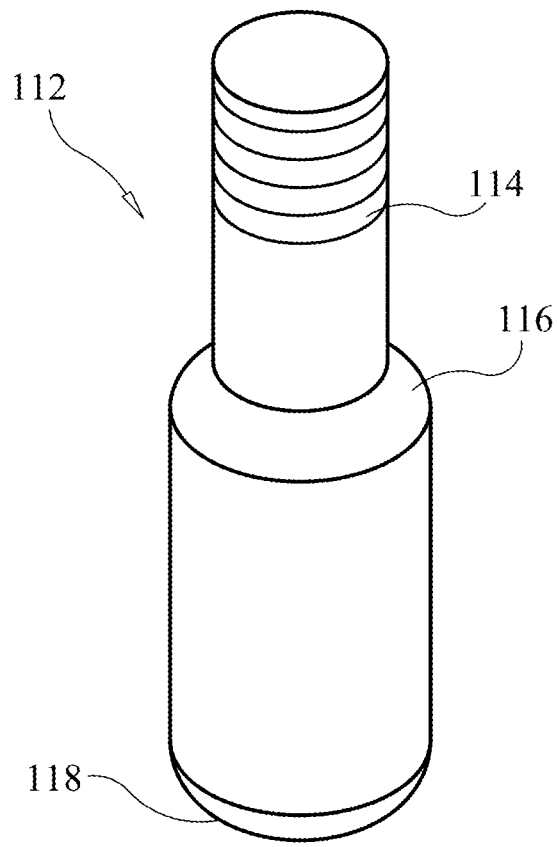
FIGS. 4A and 4B illustrate a top perspective view and a top view of an exemplary central mobile element, in accordance with an embodiment of the present disclosure.
Figure 12:
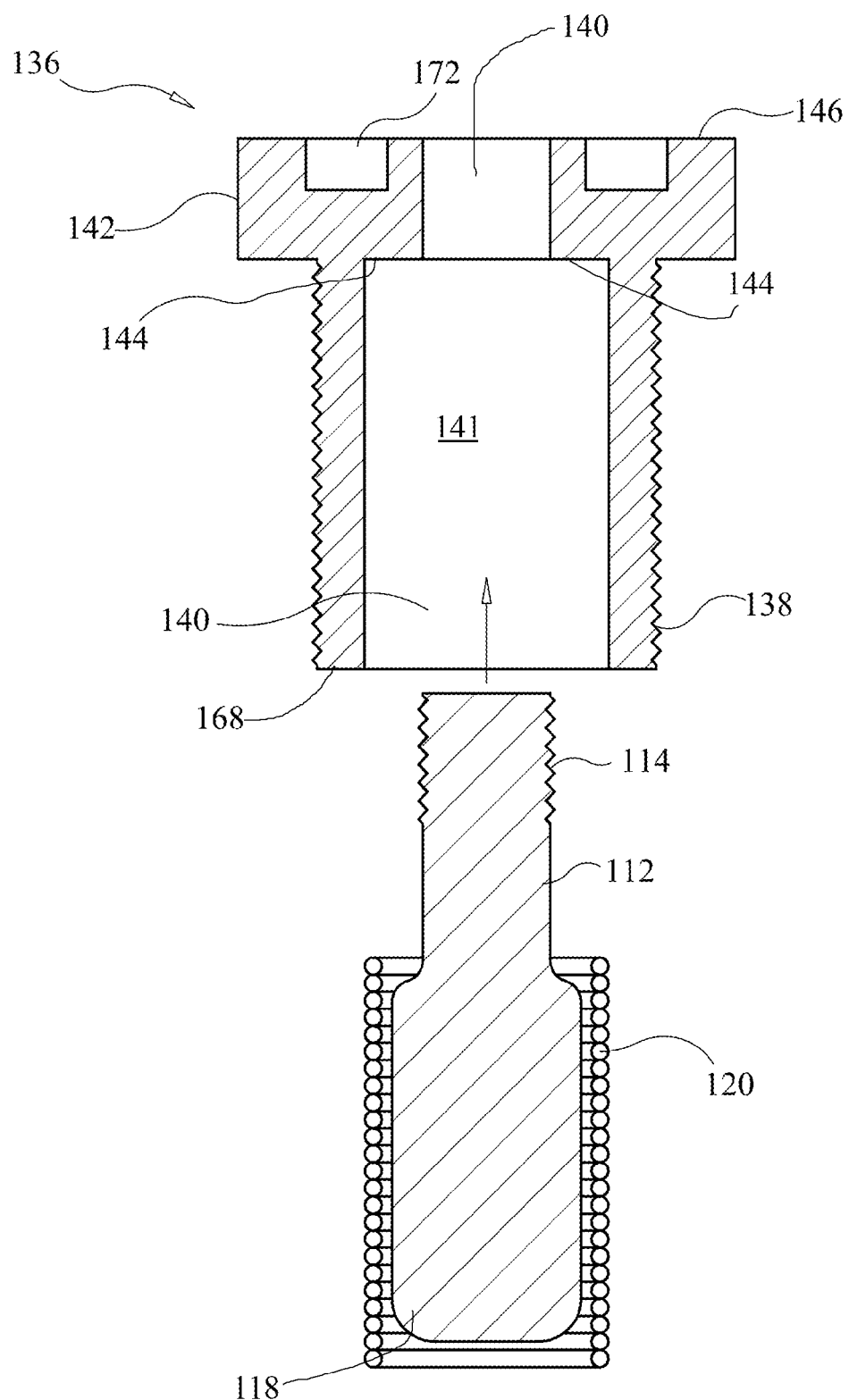
FIG. 12 illustrates a side cross sectional view of the central mobile element and the compressive coil entering a hollow chamber and an inner housing channel of the threaded cannulated housing, in accordance with an embodiment of the present disclosure.

As depicted in FIG. 1A and B, the assembly 100 comprises a central mobile element 112 that forms a vertical support for the compressive ring 134 and the compressive coil 120 to absorb and redirect the occlusal forces. As illustrated in FIG. 4A, the central mobile element 112 is provided with a shoulder portion 116 that separates the threaded superior portion 114 of the central mobile element 112 and the inferior portion 118 of the central mobile element. The central mobile element 112 has a compressive coil 120 attached to its inferior portion 118 (FIG. 12). The compressive coil 120 is operatively arranged with dimensions that provide an intimate fit along the length of the inferior portion of the central mobile element 112. The compressive coil 120 is comprised of a spring or shock absorber type of coil which provides a means of support for the inferior compression of the central mobile element 112 and via its elastic properties promotes the dissipation of functional forces applied to the central mobile element. The shoulder 116 and inferior portion 118 of the central mobile element with the attached compressive coil is geometrically confined within a hollow chamber 141 of the threaded cannulated housing 136 (FIG. 12). The shoulder 116 of the central mobile element 112 is sized and shaped with a similar taper to geometrically abut the inferior portion of the inner housing channel 140 of the threaded cannulated housing 136. The threaded cannulated housing 136 is configured with an inner housing channel 140 which is in communication with hollow chamber 141. Inner housing channel 140 is configured with a diameter to allow the superior threaded portion 114 of the central mobile element to pass through the inner housing channel 140 and threadably engage with the restorative abutment portion 126.

Figure 1B:
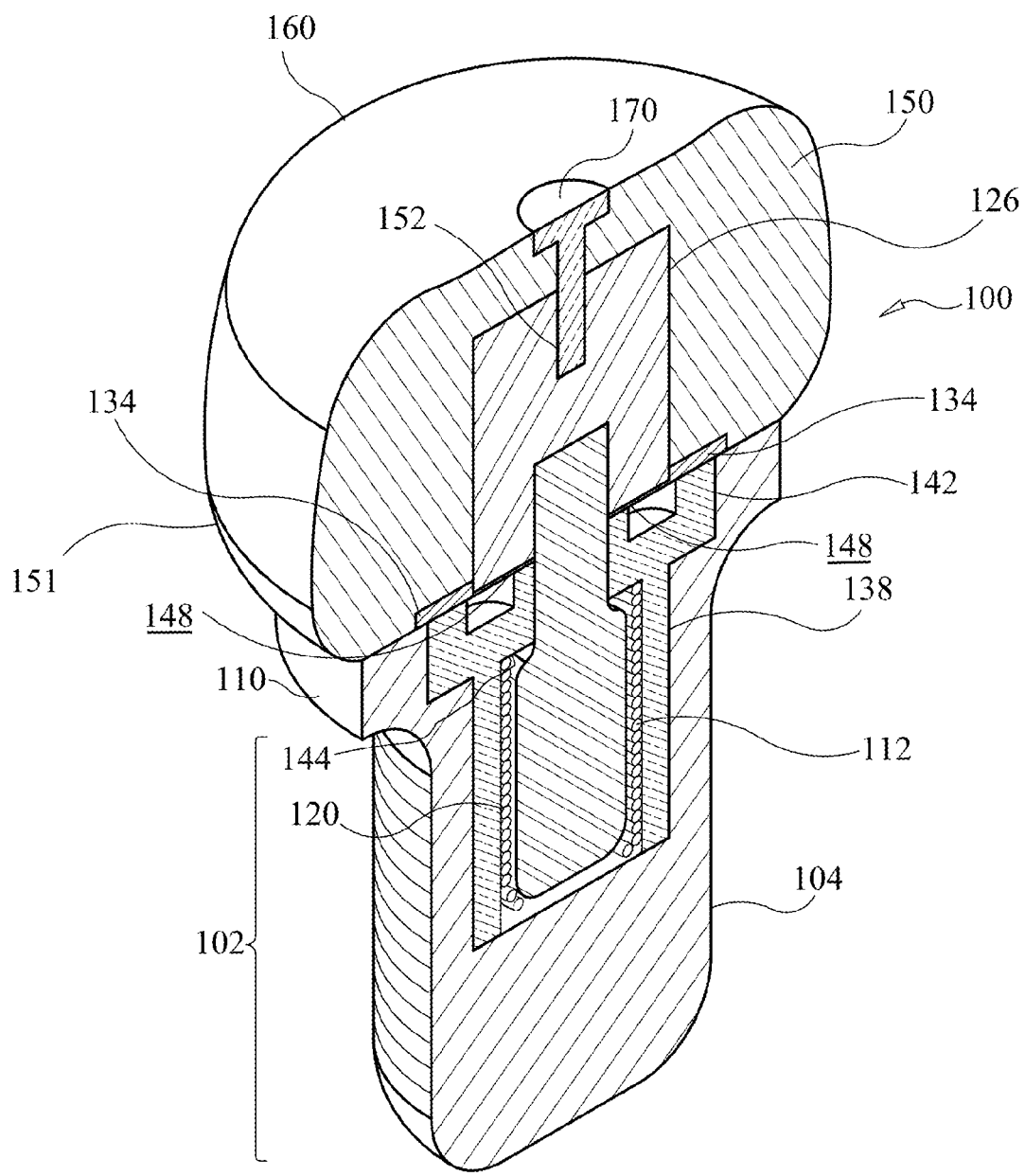
FIG. 1B illustrates a top perspective cross-sectional view of the dental implant abutment assembly, taken generally along line 1B-1B of FIG. 1A, detailing an exemplary central mobile element with a coil and an exemplary abutment portion, in accordance with an embodiment of the present disclosure.
Figure 1C:
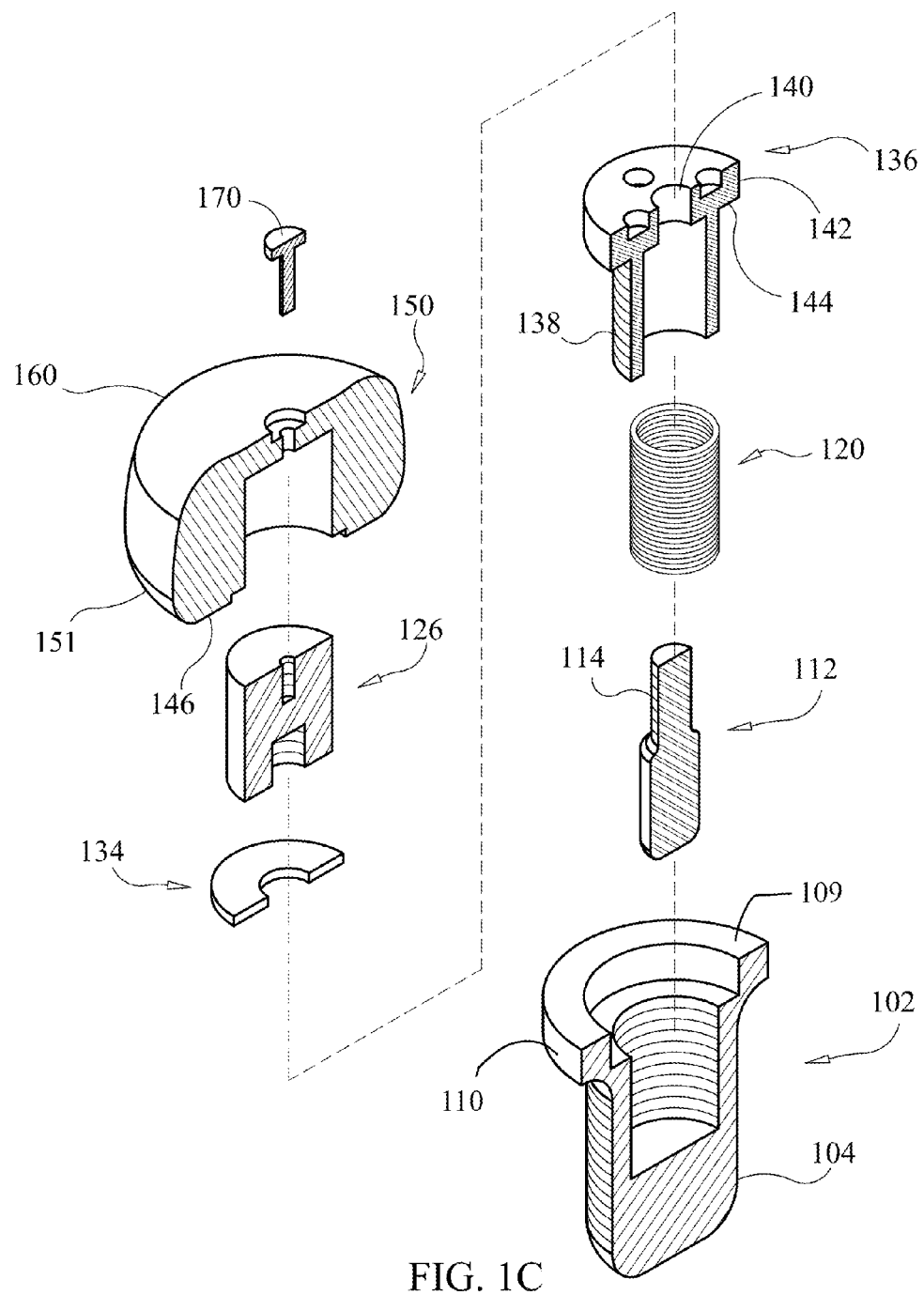
FIG. 1C illustrates a preferred embodiment of a cross-sectional exploded view of a dental implant abutment assembly for uniform distribution of occlusal forces of the present disclosure.
Figure 17:
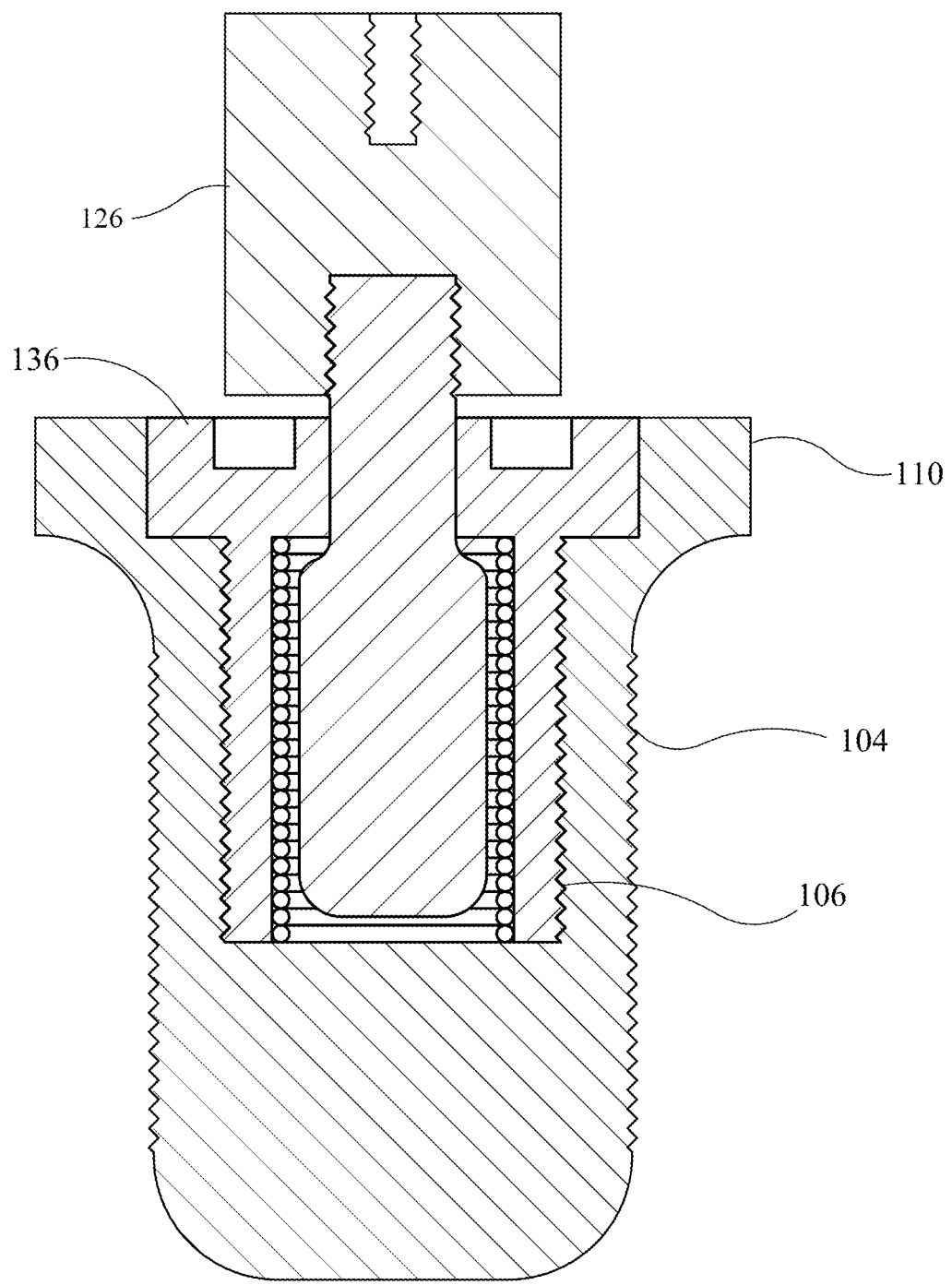
FIG. 17 illustrates a side sectional view of a restorative abutment portion attached to the superior threaded portion of the central mobile element, in accordance with an embodiment of the present disclosure.

The restorative abutment portion 126 threadably engages with the superior threaded portion 114 of the central mobile element 112 at the inferior aspect 166 of the restorative abutment's 126 inferior threaded cavity 132 (FIGS. 1B, 10, 17).

Figure 9A:
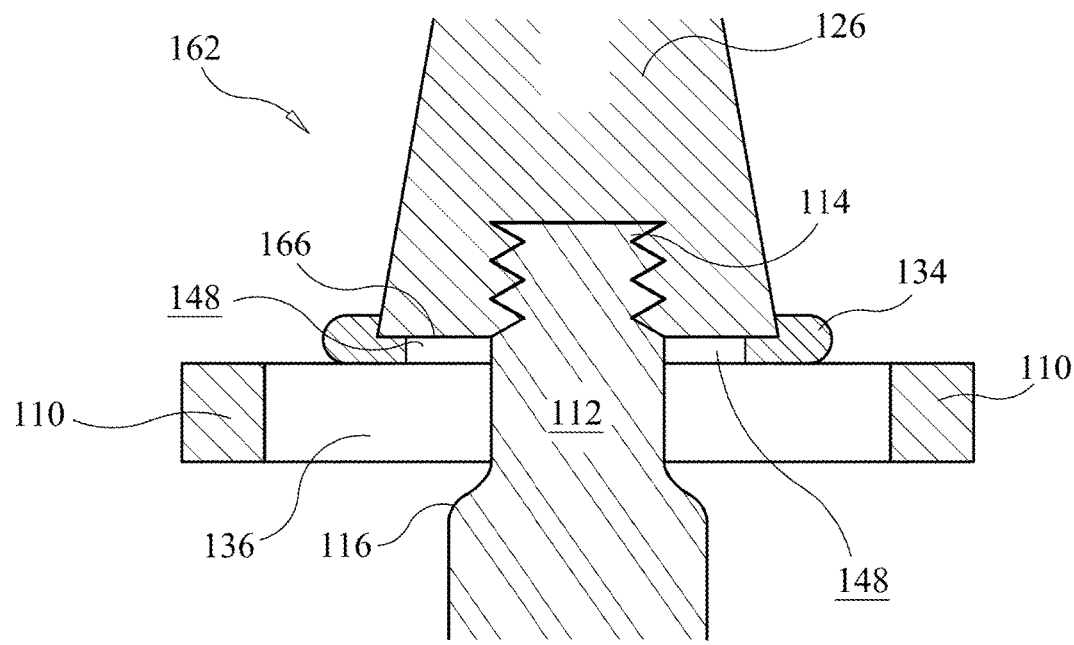
FIGS. 9A and 9B illustrate a cross-sectioned side view of a partial dental implant abutment assembly with an exemplary compression ring compressed into a loaded position and decompressed into an unloaded position, in accordance with an embodiment of the present disclosure.
Figure 9B:
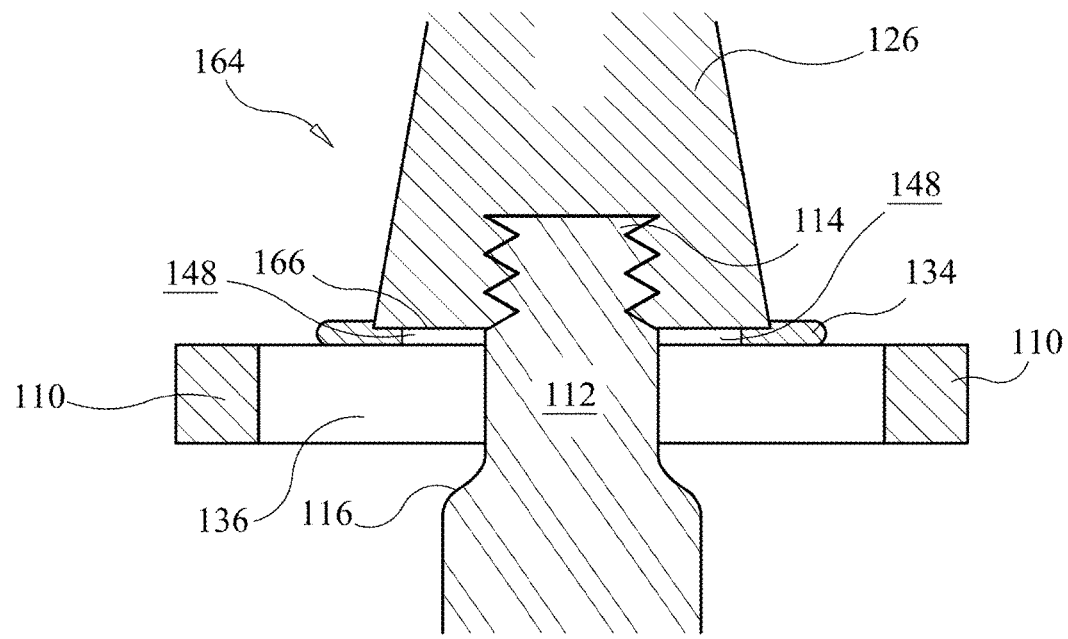

FIG. 1B illustrates a cross-sectional perspective top view of the dental implant assembly 100, taken generally along line 1B-1B of FIG. 1A, detailing an exemplary central mobile element 112 with a compressive coil 120 and an exemplary abutment portion 126, in accordance with an embodiment of the present disclosure. The assembly 100 utilizes a compressive coil 120 and a compressive ring 134 to help dampen and direct the occlusal forces towards the interior of the assembly 100. In this manner, the assembly 100 performs the same task of a periodontal ligament by allowing the prosthesis/force distribution abutment unit to compress into the body of an osseointegrated dental implant in the range of approximately 0.1 mm to 0.2 mm. The assembly 100 functions from the loaded position 164 in which the compressive ring 134 and the compressive coil 120 compress about approximately 0.1 mm to 0.2 mm, and then return to the natural unloaded position 162 (FIGS. 9A and 9B). The resilience of the compressive coil 120 and the compressive ring 134 are key factors in the componentry of the assembly for mimicking the biomechanical compressive behavior of a periodontal ligament.

Those skilled in the art will recognize that this allowable compression is generally not possible with standard dental implants. However, the dental implant abutment assembly 100 helps dissipate occlusal forces from the prosthesis/force distribution abutment unit into the body of an osseointegrated dental implant, and also on the assembly 100. In one embodiment, the assembly 100 is effective for uniformly distributing a functional force into the body of an osseointegrated dental implant, thereby reducing higher functional stresses on the cortical alveolar bone, located at the dental implant collar, to increase its viability.

In some embodiments, the assembly 100 may include a compressive ring 134 and a compressive coil 120 to absorb and redirect the occlusal forces. The compressive ring 134 and the compressive coil 120 make up a substantial portion of the force dispersion components for the force distribution abutment assembly 100. The compressive coil 120 and the compressive ring 134 enable the assembly 100 to provide a functional compressive distance in a range of about 0.1 mm to 0.2 mm for functional force distribution through the assembly 100. Specifically, the compressive ring 134 provides a dampening effect to key supportive components of the assembly 100. And the compressive coil 120 supports and redirects functional forces along a longitudinal axis of the assembly 100.

Figure 2:
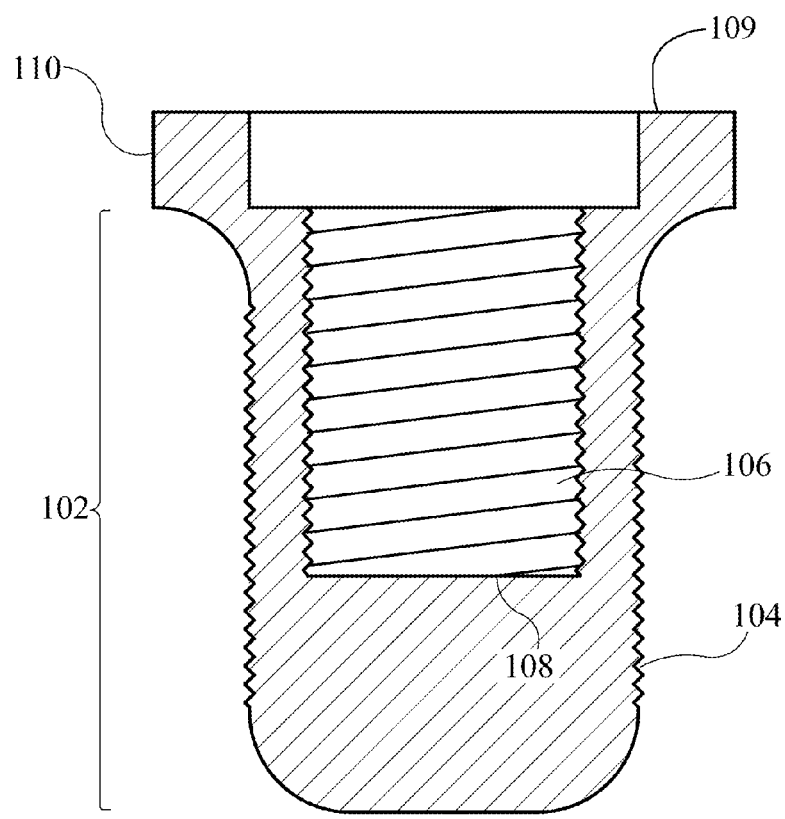
FIG. 2 illustrates a cross-sectional side view of an exemplary dental implant comprised of an implant collar, implant body, threaded external surface, and threaded central bore of a dental implant abutment assembly for uniform distribution of occlusal forces of the present disclosure.

The assembly 100 comprises a dental implant that forms an anchor for the assembly through osseointegration within the alveolar bone. FIG. 2 illustrates a cross-sectional side view of an exemplary dental implant comprised of an implant collar, implant body, threaded external surface, and threaded central bore of a dental implant assembly for uniform distribution of occlusal forces of the present disclosure. The dental implant includes the implant body 102, a collar 110, an external threaded surface 104, and an internal threaded bore 106. The collar 110 forms a restorative platform 109 for supporting a dental prosthesis 150 such as a crown and a compressive ring 134. The external threaded surface 104 threadably mounts into the native alveolar bone to form an anchor for the assembly 100.

Figure 3:
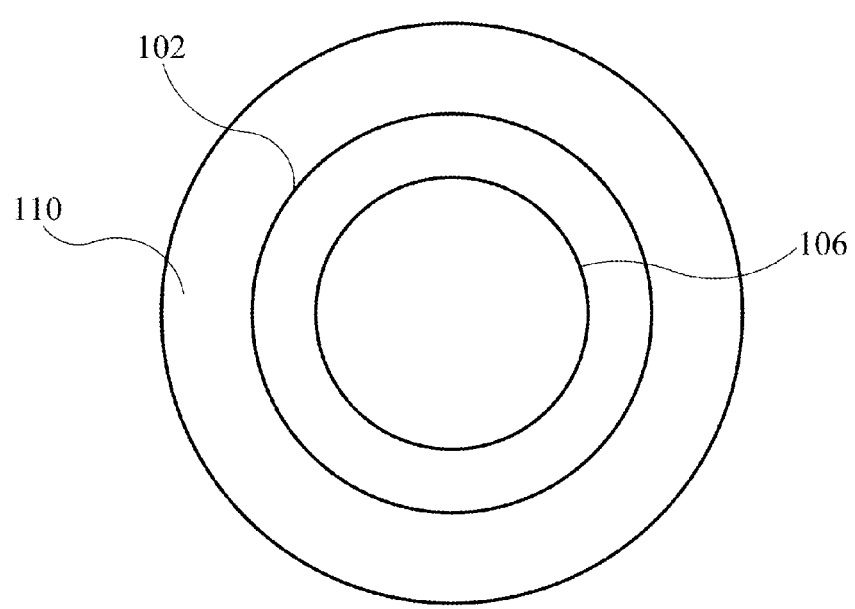
FIG. 3 illustrates a top view of an exemplary dental implant, in accordance with an embodiment of the present disclosure.

The external threaded surface 104 provides surface area for developing bone to adhere to the mechanical threads of the dental implant (FIG. 2). This biomechanical situation provides an environment for osseointegration, which helps create a rigid stability to the assembly 100, which restricts compression into the alveolar bone. This standardized situation only partially helps to uniformly distribute the occlusal forces. The internal threaded bore 106 extends along a longitudinal axis of the assembly 100 and terminates at a bore base 108. Conventionally, the occlusal forces are generally not directed into the internal threaded bore 106 of the dental implant body and components contained therein. Functional forces are more concentrated in the prosthesis, restorative platform, and cortical alveolar bone interface. Generally, the internal threaded bore 106 of the dental implant functions as a means for attaching and retaining a dental implant abutment used to support the dental prosthesis. FIG. 3 illustrates a top view of an exemplary dental implant, in accordance with an embodiment of the present disclosure.

Figure 4B:
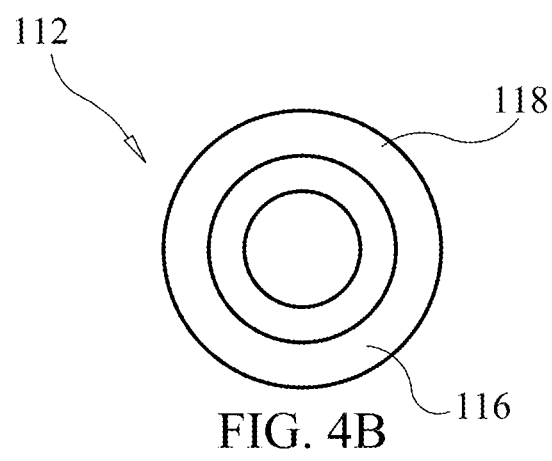

FIGS. 4A and 4B illustrate a top perspective view and a top view of an exemplary central mobile element 112, in accordance with an embodiment of the present disclosure. The central mobile element 112 is disposed to extend through the internal threaded bore 106 of the implant body 102. The central mobile element 112 is generally cylindrical and has a tapered shape. The central mobile element 112 is defined by a threaded superior portion 114, a shoulder portion 116, and an inferior portion 118. The threaded superior portion 114 is generally narrower than the inferior portion 118, as shown in FIG. 4A. The shoulder portion 116 aligns with the inferior aspect of the inner housing channel 140. The inferior portion 118 rests about 1 millimeter above the bore base 108 of the internal threaded bore 106. This bore gap enables a slight vertical displacement of the central mobile element 112, which helps dampen occlusal forces. In some embodiments, the central mobile element 112 may be fabricated from a biologically compatible, nonionizing material, including, without limitation, rubber, silicon, titanium, and titanium alloys and the like.

Figure 5:
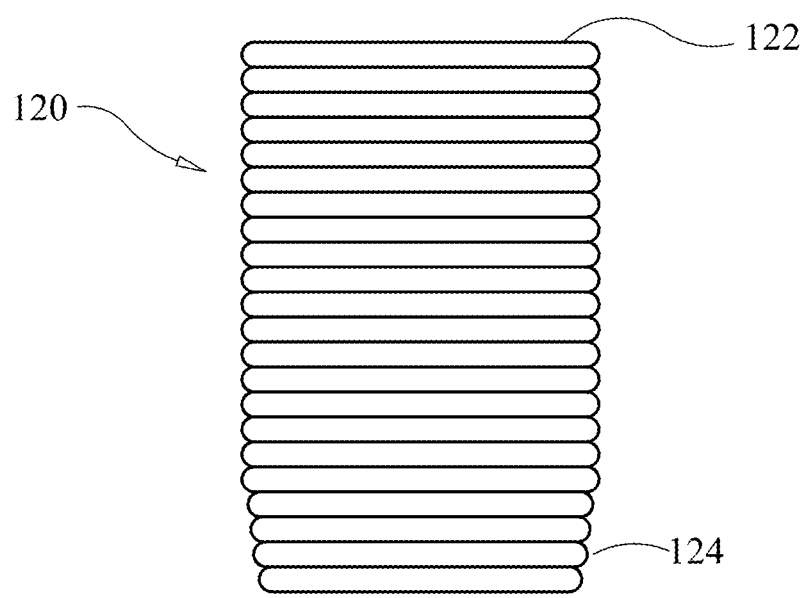
FIG. 5 illustrates a side view of an exemplary compressive coil, in accordance with an embodiment of the present disclosure.

As illustrated in FIG. 5, a compressive coil 120 is configured to wrap around the inferior portion 118 of the central mobile element 112. The compressive coil 120 is defined by a coil base 122 and an oppositely disposed coil apex 124. The compressive coil 120 extends approximately between the shoulder portion 116 at the coil base122, and the inferior portion 118 at the coil apex 124. The compressive coil 120 is one of the components that helps dampen the occlusal forces on the assembly 100. In one embodiment, the compressive coil 120 is configured to compress in the range of about 0.1 to 0.2 millimeters in the loaded position 164, and then return to a natural extended position in the unloaded position 162. Specifically, the compressive coil 120 at least partially supports vertical displacement of the central mobile element 112 for uniformly distributing occlusal forces. In one embodiment, the compressive coil 120 is stabilized in the implant body 102 by positioning within the hollow chamber 141 of the threaded cannulated housing 136. The threaded cannulated housing 136 is subsequently threaded into the internal thread bore of the dental implant 106 that is torqued into position. The compressive coil 120 may be fabricated from a biologically compatible, nonionizing material, including, without limitation, rubber, silicon, titanium, and titanium alloys and the like.

Figure 6A:
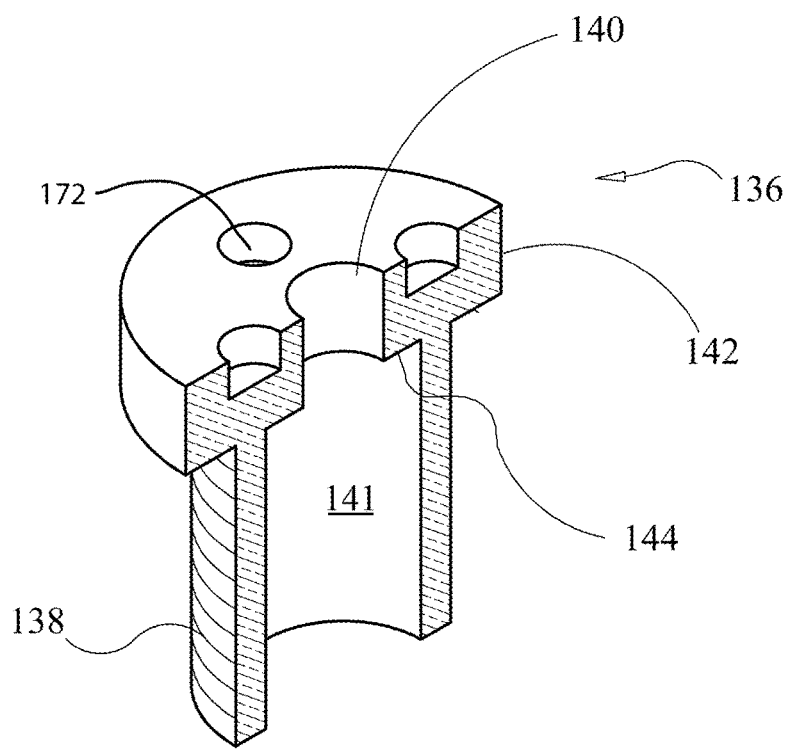
FIGS. 6A and 6B illustrate a cross sectional side view and a top view of an exemplary threaded cannulated housing with an inner housing channel, in accordance with an embodiment of the present disclosure.
Figure 6B:
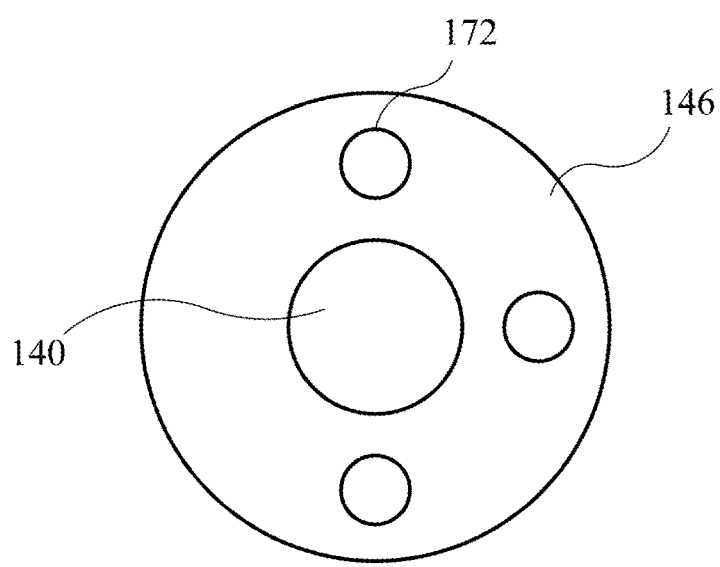

FIGS. 6A and 6B illustrate a cross sectional side view and a top view of an exemplary threaded cannulated housing with a hollow chamber and an inner housing channel, in accordance with an embodiment of the present disclosure. FIG. 6A, is a cross sectional side view of a threaded cannulated housing 136 that is configured to securely retain the central mobile element 112 and the compressive coil 120, while also firmly mounting in the implant body 102. In one embodiment, the threaded cannulated housing 136 has a hollow chamber 141 that provides a secure encasing for the central mobile element 112 and attached compressive coil 120. The threaded cannulated housing 136 comprises a hollow chamber 141 and an inner housing channel 140. As the top view of FIG. 6B illustrates, the hollow chamber 141 is configured to contain shoulder 116 and inferior portion 118 of the central mobile element 112 and the attached compressive coil 120. The inner housing channel 140 of the threaded cannulated housing 136 is tapered superiorly. This tapered configuration is arranged to restrict movement of the central mobile element 112 and the compressive coil 120 within the threaded cannulated housing 136. The threaded cannulated housing 136 also comprises an outer housing threaded surface 138. The outer housing threaded surface 138 is disposed to threadably engage the internal threaded bore 106 of the dental implant body 102. At least two depressions 172 provide a gap for a torque tool 154 to rotate the threaded cannulated housing 136. The threaded cannulated housing may be fabricated from a biologically compatible, nonionizing material including but not limited to titanium, titanium alloys, and the like.

In some embodiments, the threaded cannulated housing 136 also comprises a terminal end 168 and a locking end 142 (FIG. 12). The locking end 142 includes an inner ridge 144 and an external locking surface 146. The external locking surface 146 may have depressions 172 that enable a torque tool 154 to rotatably engage the threaded cannulated housing 136, such that the threaded cannulated housing 136 passes through the internal threaded bore 106 of the implant body 102. As illustrated in FIG. 6A this embodiment of the assembly 100 includes three depressions 172, however it should be understood that any number of depressions to securely adapt a torque tool to manipulate the cannulated housing could be used. The inner ridge 144 of the locking end 142 engages the inferior portion of the dental implant collar 110 in the superior aspect of the threaded internal bore 106 of the dental implant. In one embodiment, a functional space 148 forms between the threaded superior portion 114 of the central mobile element 112 and the external locking surface 146 of the threaded cannulated housing 136. The functional space 148 provides additional flexibility and resilience to the assembly 100 under applied functional forces.

Figure 7A:
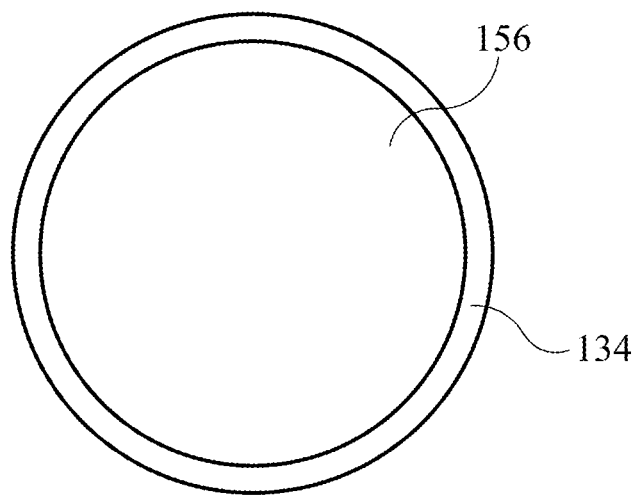
FIGS. 7A and 7B illustrate a top view and a side view of an exemplary compressive ring, in accordance with an embodiment of the present disclosure.
Figure 7B:
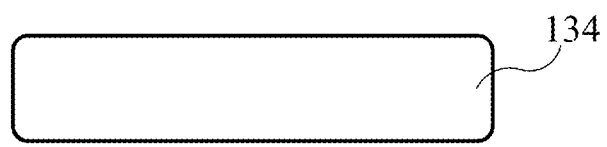

FIGS. 7A and 7B illustrate a top view and a side view of an exemplary compressive ring, in accordance with an embodiment of the present disclosure, the compressive ring 134 that helps dampen occlusal forces on the assembly 100. The compressive ring 134 is placed at the junction between a dental prosthesis 150 and the collar 110/restorative platform 109 of the dental implant. The compressive ring 134 allows compression during application of functional loads to the dental prosthesis 150 and promotes dissipation vertical, angular and horizontal forces at the junction between the dental prosthesis 150 and the restorative platform 109. The compressive ring 134 has a central hole 156 and is generally manufactured from resilient material composition. The threaded superior portion 114 is sized to pass through the central hole 156 of the compressive ring 134.

Figure 8:
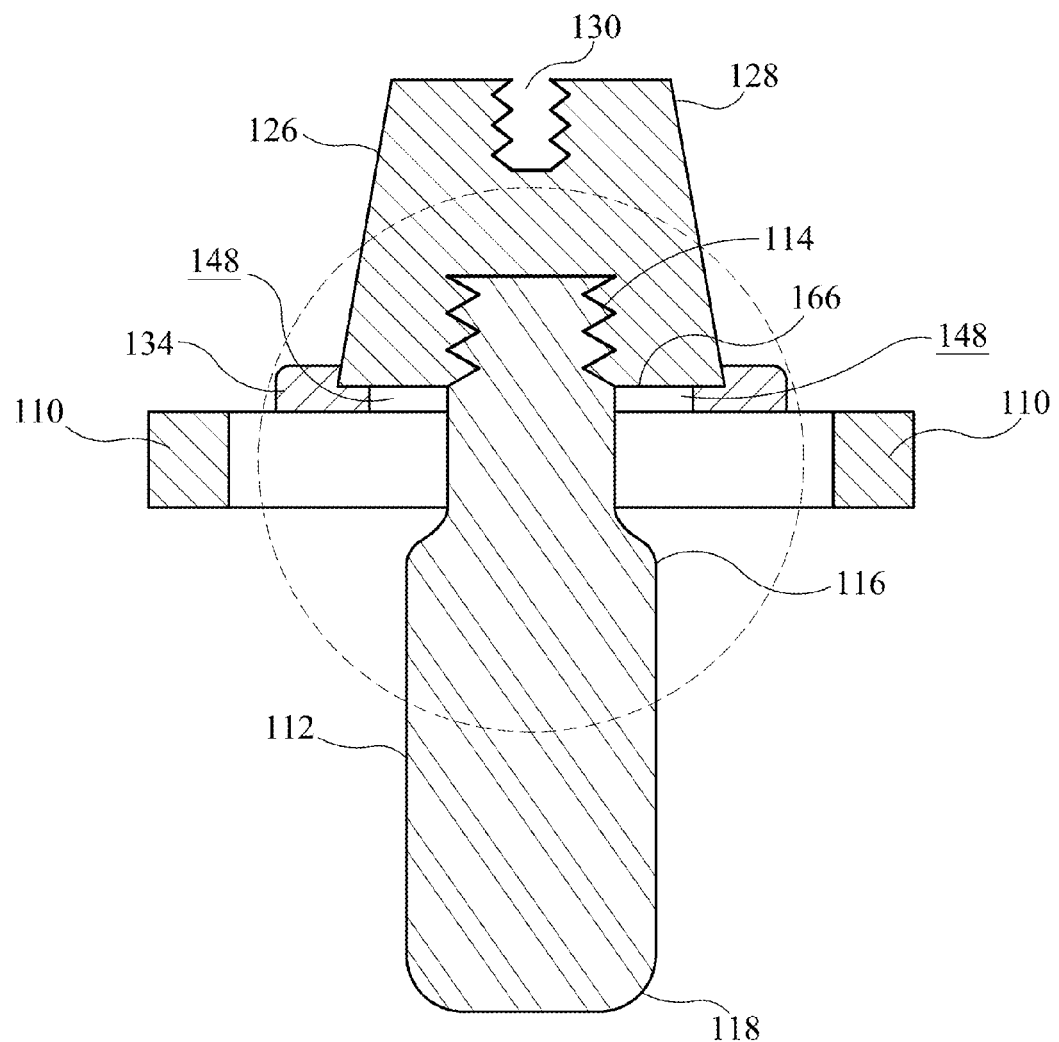
FIG. 8 illustrates a cross-sectioned side view of a partial dental implant abutment assembly depicting the space between the restorative abutment portion and the restorative collar of the dental implant, in accordance with an embodiment of the present disclosure.

FIG. 8 illustrates a cross-sectioned side view of a partial dental implant abutment assembly depicting the functional space 148 between the restorative abutment portion and the restorative collar of the dental implant, in accordance with an embodiment of the present disclosure. In one embodiment, the compressive ring 134 is stretched taut over the restorative abutment portion 126 and advanced inferiorly until it intimately contacts the external locking surface 146 of the threaded cannulated housing 136 and a portion of the inferior aspect 166 of the restorative abutment portion 126. This positioning helps the compressive ring 134 restrict moisture in the functional space 148 between the threaded superior portion 114 of the central mobile element 112 in the external locking surface 146 of the threaded cannulated housing 136. The compressive ring 134 substantially, but not completely, occupies the functional space 148 formed between the inferior aspect of the threaded superior portion 114 of the central mobile element 112 in the external locking surface 146 of the threaded cannulated housing 136. The compressive ring 134 is configured to compress in a range of about 0.1 mm to 0.2 mm. In one embodiment, the compressive ring 134 is about 1.5 mm to 2.0 mm in height and about and about 1.0 mm in thickness. The compressive ring 134 may be fabricated from a biologically compatible, non-ionizing material, including but not limited to rubber, silicone, foam and resilient polymers and the like.

Those of ordinary skill in the art will recognize that the compressive ring 134 and the compressive coil 120 enable the assembly 100 to have a compressive force dissipation capability similar to that permitted by the periodontal ligament with regard to natural teeth. This force dissipation provides greater success for restorations that potentially combine dental implants and natural teeth as abutments within the same restoration or in circumstances where anatomical limitations (i.e. inferior alveolar nerve, maxillary, sinus etc.) dictate placement of shorter implants. While a natural tooth has a periodontal ligament to provide the means for compressive force distribution, the force distribution of the compressive ring 134 and the compressive coil 120 provide the necessary 0.1 mm to 0.2 mm of compressive force distribution for a restored dental implant through two systems working simultaneously under function.

The compressive ring 134 absorbs and dampens vertical, horizontal, and angular forces applied onto the assembly 100 from a loaded position 164 (FIG. 9A), and then relaxes into an unloaded position 162 (FIG. 9B). The compressive ring 134 is configured to compress between about 0.1 mm to 0.2 mm in the loaded position 164. This biomechanical force distribution creates a great advantage over a conventional rigid restoration of an implant, which concentrates functional stress at the alveolar crest, by utilizing the greater pliability and microvascular stability of the cancellous alveolar bone, in which the body of the dental implant resides and where the functional forces are being directed.

Figure 10A:
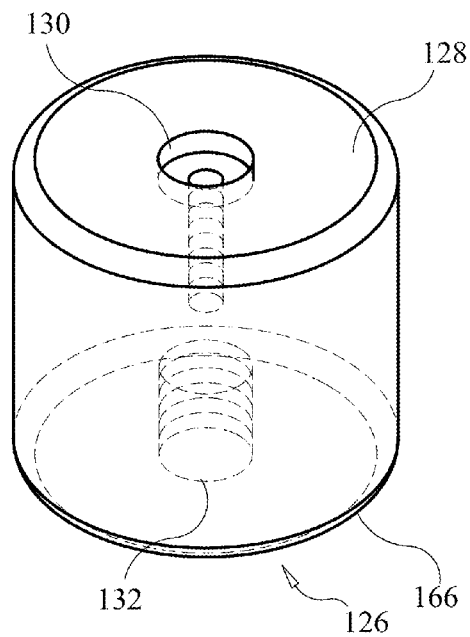
FIGS. 10A and 10B, illustrate a top perspective view and a top cross-sectional view of an exemplary restorative abutment portion having a broad superior aspect of the restorative abutment portion.
Figure 10B:
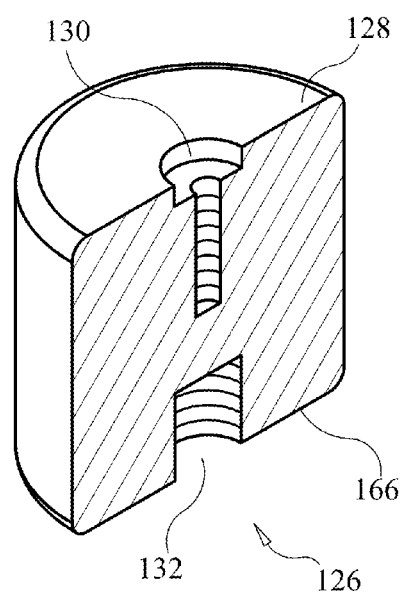
Figure 10C:
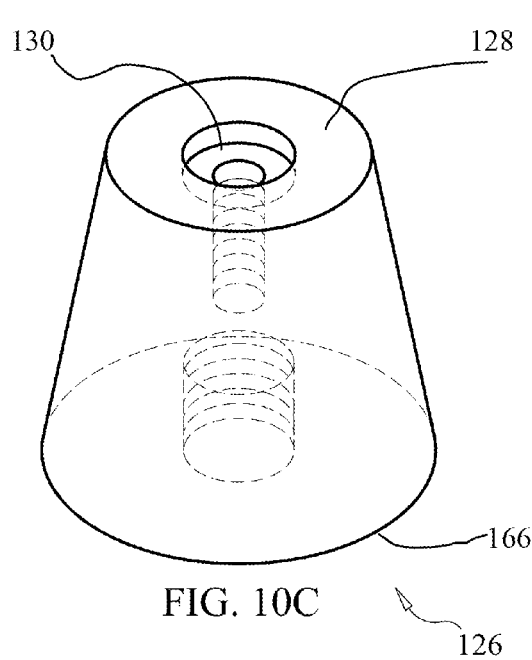
FIGS. 10C and 10D illustrate a top perspective view and a top cross-sectional view of another exemplary restorative abutment portion having a narrow superior aspect of the restorative abutment portion.
Figure 10D:
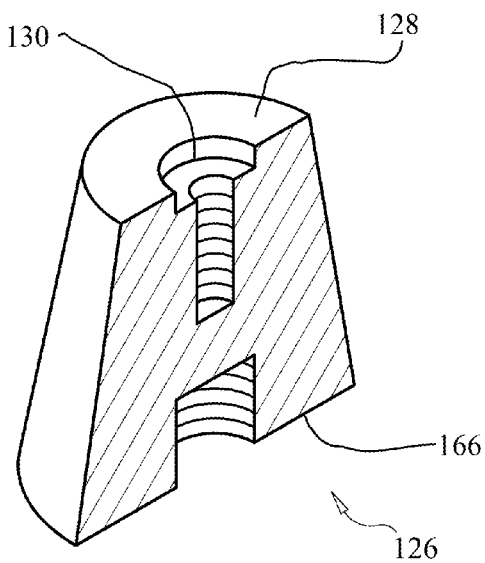

FIGS. 10A and 10B, illustrate a top perspective view and a top cross-sectional view of an exemplary restorative abutment portion 126 having a broad superior aspect of the restorative abutment portion. FIGS. 10C and 10D illustrate a top perspective view and a top cross-sectional view of another exemplary restorative abutment portion 126 having a narrow superior aspect of the restorative abutment portion;

The abutment portion 126 is configured to attach the central mobile element 112 to the dental prosthesis 150. The restorative abutment portion 126 is defined by an inferior aspect 166 having an inferior threaded cavity 132 and a superior aspect 128, having a threaded central region 130 (FIG. 10B). The inferior aspect 166 of the restorative abutment portion 126 is disposed to engage the compressive ring 134 positioned inferiorly on the collar 110 of the dental implant. The compressive ring 134 helps dampen occlusal forces of the restorative abutment portion 126. The inferior threaded cavity 132 of the restorative abutment portion 126 is threaded to threadably attach to the superior portion of the central mobile element. The threaded configuration is effective for rotatably engaging the threaded superior portion 114 of the central mobile element 112, such that the restorative abutment portion 126 can be depressed inferiorly with the external support of the compressive ring 134. Furthermore, to create a more efficient assemblage, the inferior threaded cavity 132 of the restorative abutment portion 126 is threaded to a compatible pitch with the threads of the threaded superior portion 114 of the central mobile element 112.

Those of ordinary skill in the art will recognize the potential platform switching design provided by the restorative portion of the abutment 126 would provide an accepted means to further decrease alveolar bone resorption along the collar of the dental implant which has a tendency to occur at a rate of approximately 1.0 mm in the first year, and 0.1 mm each year until functional stabilization of the bone and implant body 102 interface has been established. The restorative abutment portion 126 may be fabricated from a biologically compatible, nonionizing material, including but not limited to, rubber, silicone, titanium and titanium alloys and the like. The restorative abutment portion 126 is configured to seat onto the compressive ring 134 and also forms a base of support for the dental prosthesis 150. In some embodiments, the width of the base can be increased or decreased to accommodate different occlusal schemes and configurations of dental prostheses 150.

FIGS. 10A, 10B, 10C, and 10D illustrate an exemplary restorative abutment portion with narrow and broad superior aspect 128. While both the broad and narrow versions of the restorative abutment portion 126 function in generally the same manner, FIGS. 10C and 10D illustrate a more tapered superior aspect 128 of the restorative abutment portion 126 relative to inferior aspect 166, while FIGS. 10A and 10B illustrate a broader diameter of surface area for the superior aspect 128 of the restorative abutment portion 126 relative to the tapered superior aspect depicted in FIG. 10 C and D. The broad inferior aspect 166 provides a wide base to support the compressive ring 134. The diameter of the superior aspect 128 depicted in FIGS. 10A-D depend on the size of the dental prosthesis 150 that is to be attached to the restorative abutment portion 126 for the given occlusal scheme, the restorative abutment dimensions are based on the restorative situation presented.

Consequently, the combination of force distribution from the compressive ring 134, the compressive coil 120, the functional space 148 beneath the threaded superior portion 114, and the bore gap between the central mobile element 112 and the bore base 108 allows the abutment 126 to compress the central mobile element in a range of about 0.1 mm to 0.2 mm within the internal threaded bore 106 of the dental implant body 102 under functional loading. Additionally, occlusal forces are directed along the longitudinal axis of the central mobile element 112 where functional loading is best tolerated. The cumulative effect of each component in the assembly 100, thus forms a micro-motion mechanism that imitates the biomechanical parameters provided by the periodontal ligament as it pertains to natural teeth.

After the abutment portion 126 has been attached, a dental prosthesis 150 is incorporated into the restorative abutment portion 126. The dental prosthesis 150 is composed of biomechanical materials (porcelain, noble metals, gold, etc. and the like) which possess inherent physical properties (modulus of elasticity, compression strength, sheer strength, etc.) which transmit functional forces from opposing structures by compression and flexure of the materials along the abutment assembly and against the rigid restorative platform 109 initiating the function of the entire assembly and its componentry. The dental prosthesis 150 is defined by a prosthesis cavity 152, an occlusal surface 160 and a restorative margin 151 that is disposed to engage the collar 110/restorative platform 109 of the implant body 102.

In one embodiment, the dental prosthesis 150 is screwed onto the abutment 126 with a retention screw 170 that rotatably passes through the prosthesis cavity 152. In this manner, functional forces that are applied to the dental prosthesis 150 during occlusion are distributed through the restorative abutment portion 126, and finally on to the central mobile element 112. The retention screw 170 may be used to attach the dental prosthesis 150 onto the superior aspect 128 of the abutment 126, whereby retention screw 170 rotatably engages the central threaded area 130 of the superior aspect 128 of the restorative abutment portion 126. A common torque tool may be used to tighten the dental prosthesis 150 onto the abutment 126.

Figure 11:
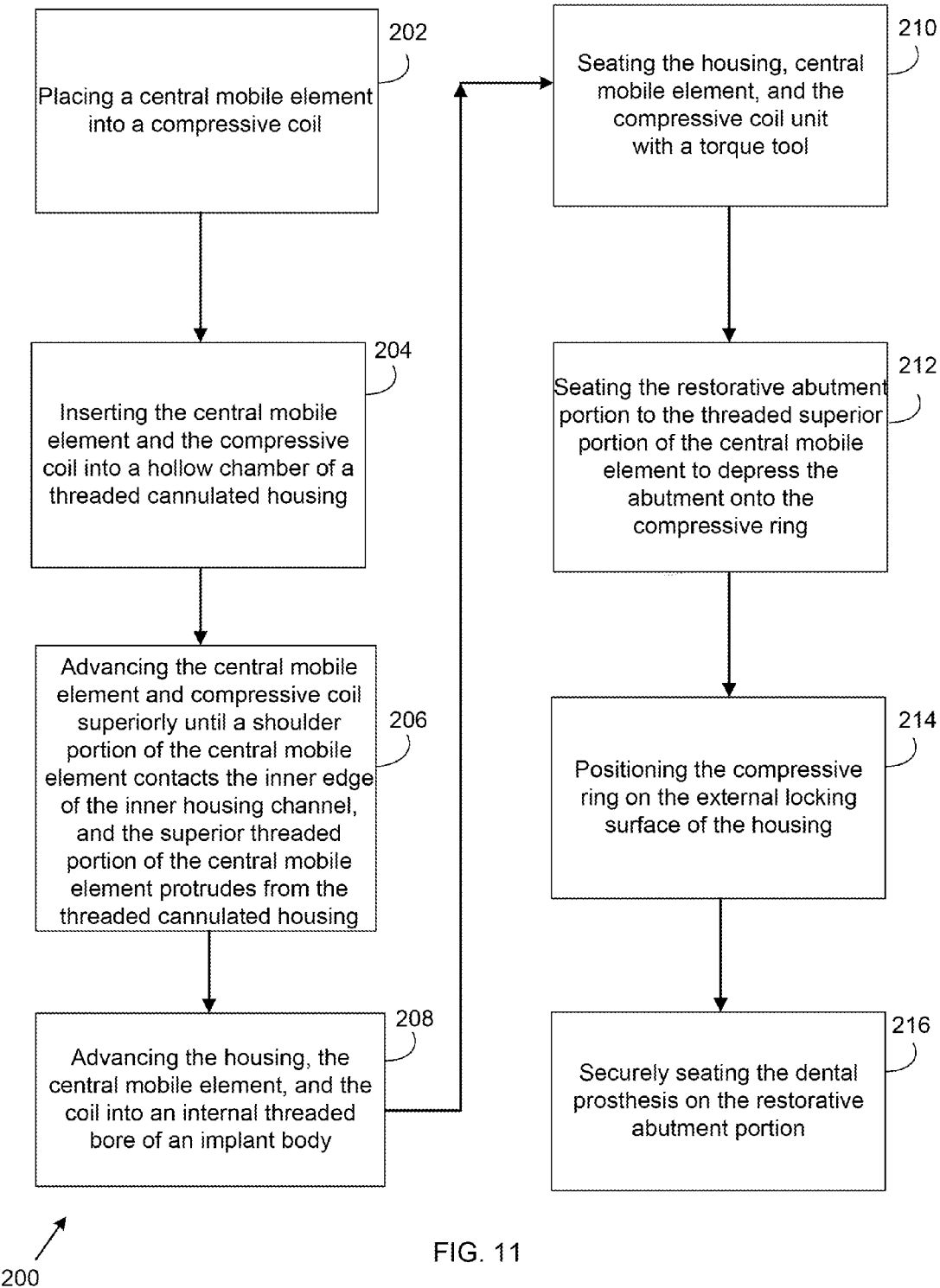
FIG. 11 illustrates a flowchart diagram of an exemplary method for uniformly distributing occlusal forces with a dental implant abutment assembly, in accordance with an embodiment of the present disclosure.

FIG. 11 illustrates a flowchart diagram of an exemplary method 200 for uniformly distributing occlusal forces utilizing dental implant abutment assembly 100, in accordance with an embodiment of the present disclosure for uniformly distributing occlusal forces within a dental implant abutment assembly 100 utilizing a compressive coil 120 and a compressive ring 134 to dampen and direct the occlusal forces towards the interior of the assembly 100. The assembly 100 forms a micro-motion mechanism configured to imitate the biomechanical behavior of the periodontal ligament through a compressive action that dampens vertical, horizontal, and angular forces applied to the assembly 100. The occlusal forces are generally directed into the interior of the assembly 100. In this manner, the assembly 100 performs the same task of a periodontal ligament by allowing the prosthesis/force distribution abutment unit to compress into the body of an osseointegrated dental implant in the range of approximately 0.1 mm to 0.2 mm.

FIG. 11 illustrates a flowchart diagram of an exemplary method 200 for installing a dental implant abutment assembly 100. The method 200 includes an initial Step 202 of placing the central mobile element 112 into the compressive coil 120. The coil base 122 is aligned superiorly to the shoulder portion 116 of the central mobile element 112, and the coil apex 124 of the compressive coil 120 covers the inferior portion 118 of the central mobile element 112, as shown in FIG. 1B. In some embodiments, a Step 204 may then include inserting the central mobile element 112 and the compressive coil 120 into the hollow chamber 141 of the threaded cannulated housing 136, as shown in FIG. 12. FIG. 12 illustrates a side cross sectional view of the central mobile element and the compressive coil entering the hollow chamber 141 of the threaded cannulated housing 136 in accordance with an embodiment of the present disclosure.

The central mobile element 112 and compressive coil 120 are introduced into the threaded cannulated housing 136 with the threaded superior portion 114 of the central mobile element 112 being passed through the narrowest section of the inner housing channel 140.

A Step 206 includes advancing the central mobile element 112 and compressive coil 120 superiorly until the shoulder portion 116 of the central mobile element 112 contacts the inner ridge 144 on the locking end 142 of the threaded cannulated housing 136. This maneuver results in the threaded superior portion 114 of the central mobile element 112 extending superiorly beyond the superior most portion of the external locking surface 146 of the threaded cannulated housing 136. The insertion of the central mobile element 112 and compressive coil 120 into the hollow chamber 141 is completed when the inferior most threaded portion of the threaded superior portion 114 of the central mobile element 112 is approximately 1.0 mm above the most superior portion of the external locking surface 146. The shoulder portion 116 and the inferior portion 118 of the central mobile element 112 and the compressive coil 120 are now contained within the hollow chamber 141 and inner housing channel 140 of the threaded cannulated housing 136.

Figure 13:
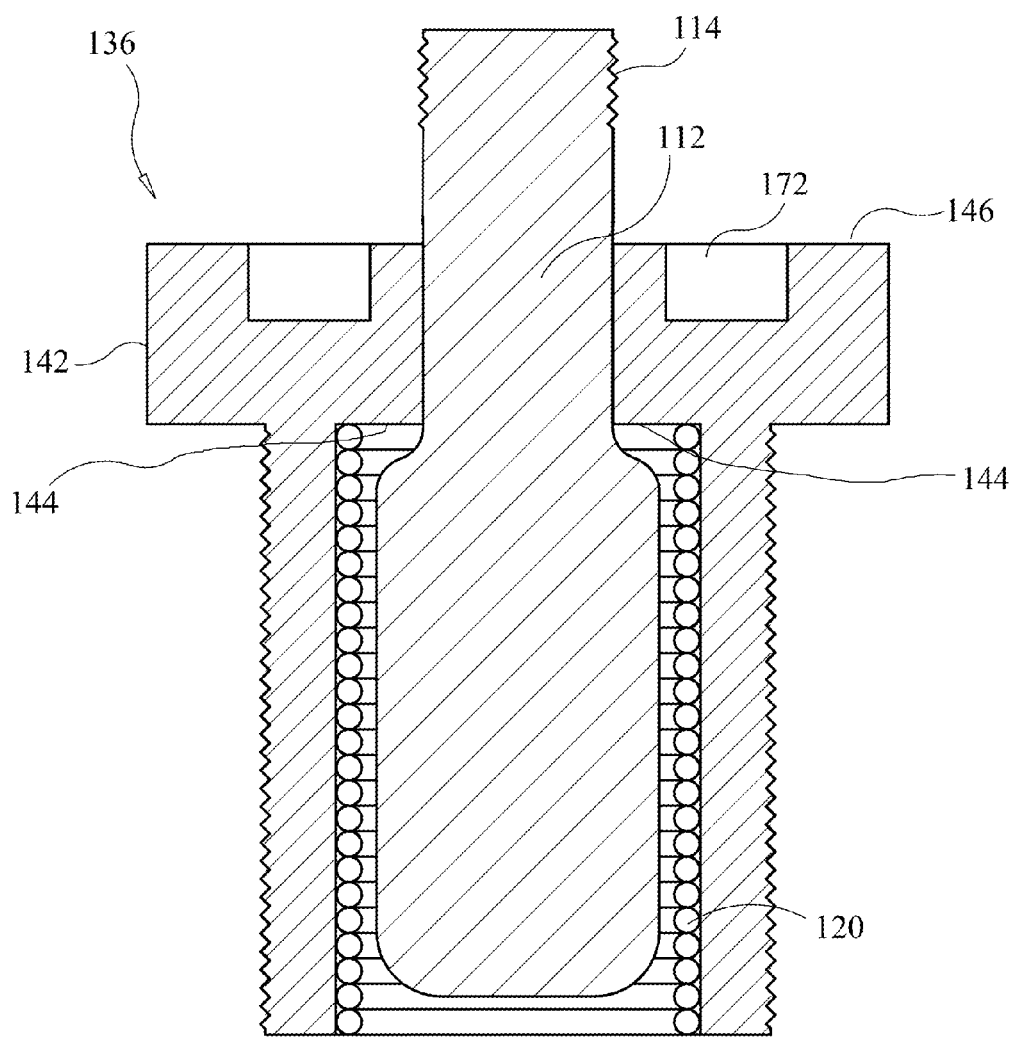
FIG. 13 illustrates a side sectional view of the central mobile element and the compressive coil seated inside the hollow chamber and the inner housing channel of the threaded cannulated housing with the superior threaded portion of the central mobile element protruding from the inner housing channel, in accordance with an embodiment of the present disclosure.
Figure 16:
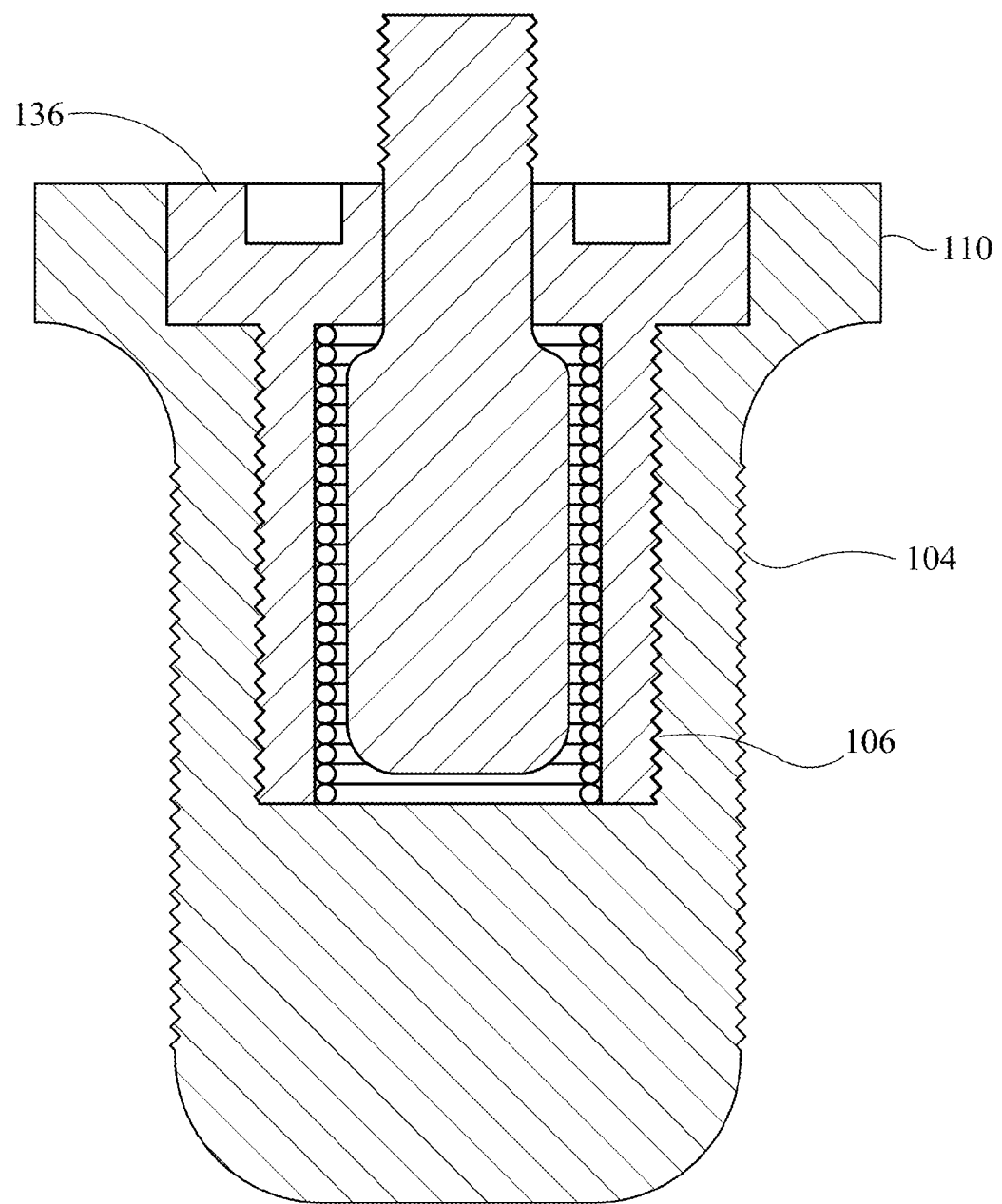
FIG. 16 illustrates a side sectional view of the threaded cannulated housing, containing the central mobile element and the compressive coil, seated inside the implant body and central threaded bore of the dental implant, in accordance with an embodiment of the present disclosure.

From this inserted position, the compressive coil 120 occupies the region between the vertical walls and base of the inferior housing channel of the threaded cannulated housing 136 and the central mobile element 112, and thus a single functional unit is formed. In some embodiments, a Step 208 may further include advancing the threaded cannulated housing 136, the central mobile element 112, and the compressive coil 120 into the internal threaded bore 106 of the dental implant body 102. The threaded cannulated housing 136, central mobile element 112, and compressive coil 120, are now compiled as a single functional unit and advanced into the implant body 102, as illustrated in FIGS. 16 and 17. FIG. 13 illustrates a side sectional view of the central mobile element and the compressive coil seated inside the inner housing channel of the threaded cannulated housing, in accordance with an embodiment of the present disclosure.

Figure 14:
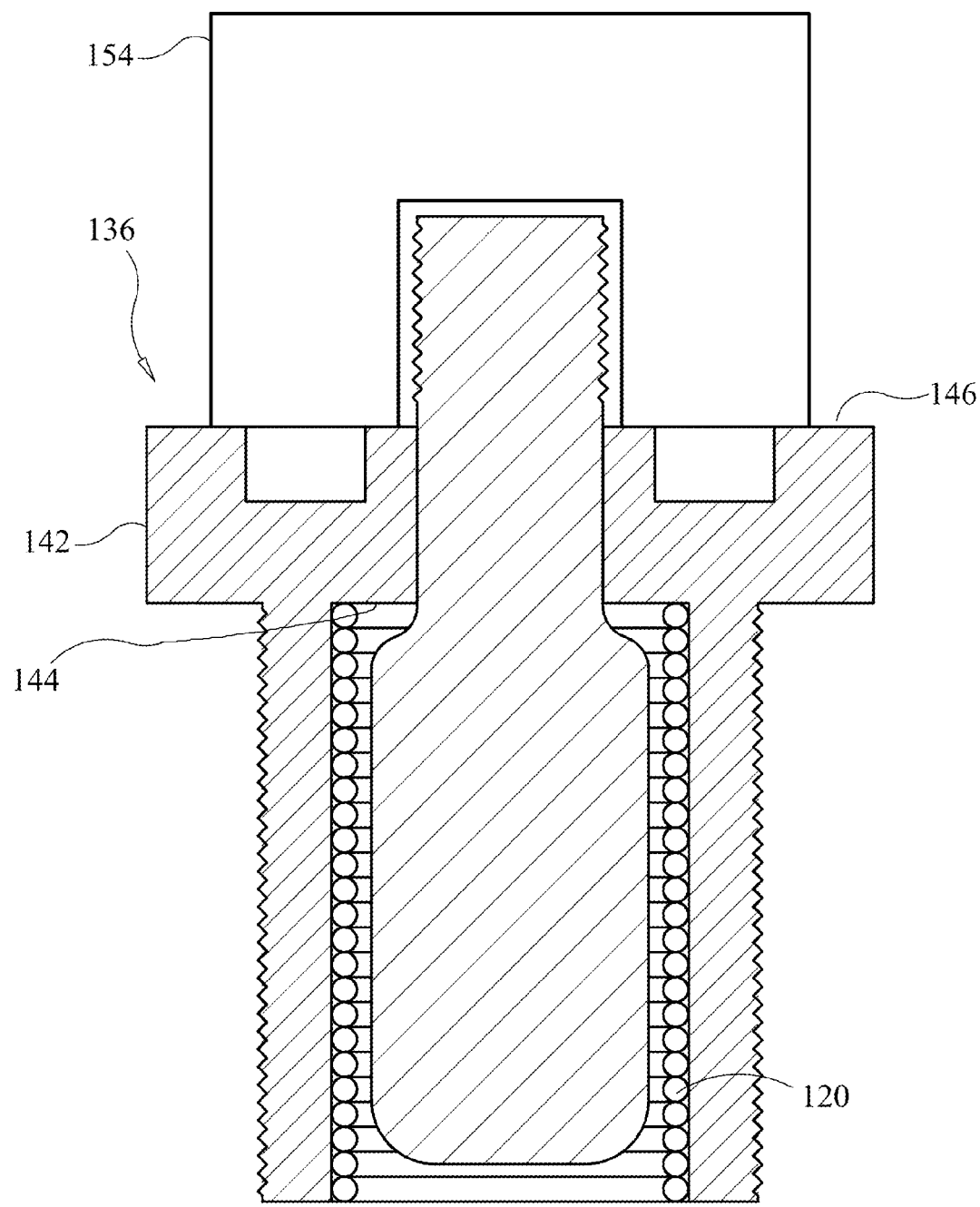
FIG. 14 illustrates a side sectional view of an exemplary torque tool rotatably engaging an external locking surface of the housing, in accordance with an embodiment of the present disclosure.

A Step 210, shown in FIG. 14, includes inserting the threaded cannulated housing 136, central mobile element 112, and compressive coil 120 with a torque tool 154. FIG. 14 illustrates a side sectional view of an exemplary torque tool rotatably engaging an external locking surface 146 of the housing, in accordance with an embodiment of the present disclosure. As shown in FIG. 14, this unit is securely positioned into the internal threaded bore 106 of the osseointegrated dental implant via a torque tool 154 firmly seated into the three depressions on the external locking surface 146 of the threaded cannulated housing 136. In some embodiments, the complete seating of the threaded cannulated housing 136, the central mobile element 112, and the compressive coil 120 unit may be confirmed by radiographic examination.

Figure 15:
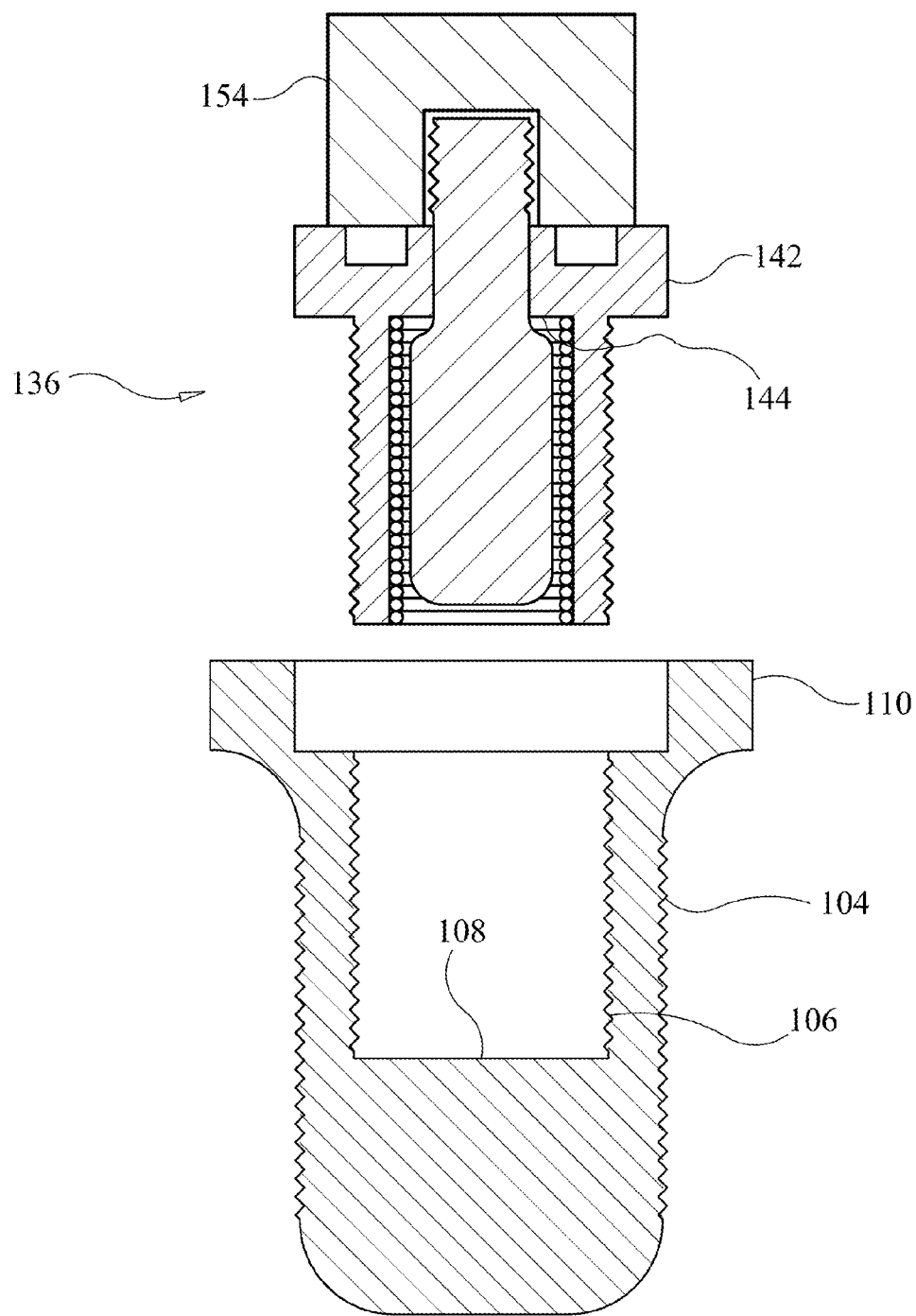
FIG. 15 illustrates a side sectional view of the threaded cannulated housing entering an internal threaded bore of the implant body, in accordance with an embodiment of the present disclosure.

FIG. 15 illustrates a side sectional view of the threaded cannulated housing 136 lined up to enter an internal threaded bore 106 of the implant body 102, in accordance with an embodiment of the present disclosure. Once the seating of threaded cannulated housing 136 with the central mobile element 112, and attached compressive coil 120 is confirmed, a manufacturer's suggested final torque would be applied by the torque tool 154 to secure the threaded cannulated housing 136, the central mobile element 112, and the compressive coil 120 unit into the internal threaded bore 106 of the implant body 102 and prevent rotational forces from unthreading the unit from the internal threaded bore 106 of the implant body 102. FIG. 16 illustrates a side sectional view of the threaded cannulated housing, containing the central mobile element and the compressive coil, seated inside the implant body and central threaded bore of the dental implant, in accordance with an embodiment of the present disclosure;

After the threaded cannulated housing 136, central mobile element 112, and compressive coil 120 are torqued into the final position, the superior horizontal component of the threaded cannulated housing 136 may be flush with the collar 110 of the osseointegrated dental implant, or the horizontal component of the threaded cannulated housing 136 may extend 1.0 mm above the collar 110 depending on the presenting restorative and occlusal situation (not shown). The central mobile element's 112 threaded superior portion 114 most inferior aspect extends above the external locking surface 146 of the threaded cannulated housing 136 and the collar 110 of the dental implant by about 1.0 mm (FIG. 17).

Figure 18:
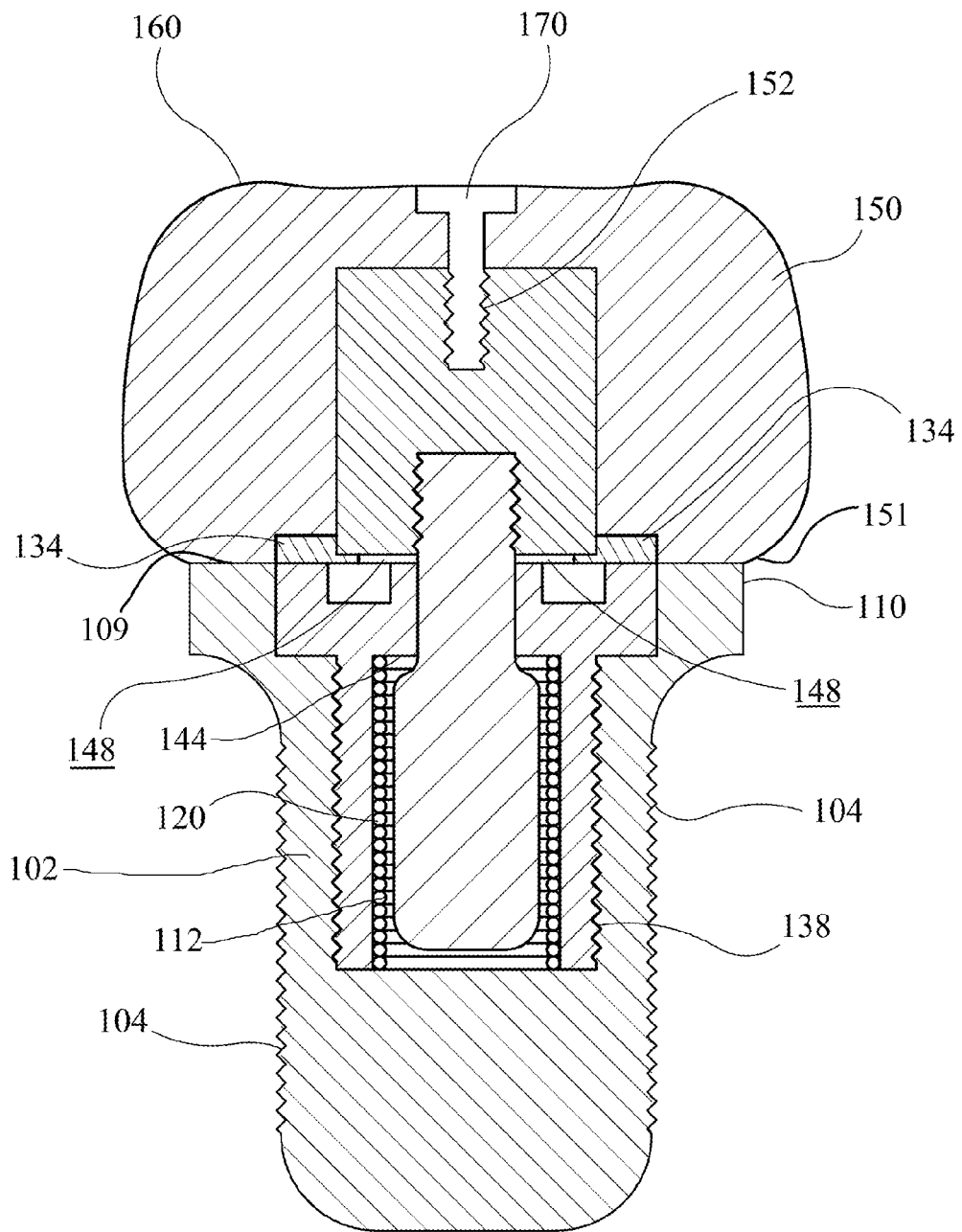
FIG. 18 illustrates a side cross-sectional view of an exemplary screw rotatably engaging a cavity in the dental prosthesis connecting the prosthesis to the restorative abutment portion and the restorative collar of the dental implant, in accordance with an embodiment of the present disclosure.

A Step 212 includes seating the restorative abutment portion 126 to the threaded superior portion 114 of the central mobile element 112 to permit depression of the abutment 126 with the external support of the compressive ring 134 (FIG. 18). In one embodiment, the abutment 126 is threaded on to the threaded superior portion 114 of the central mobile element 112. Once the restorative abutment portion 126 is seated, on to the threaded superior portion 114 of the central mobile element 112, a manufacturer's recommended torque can be applied using the appropriate torque tool 154 to prevent the rotation of the abutment 126 while under functional forces from its secured position on the central mobile element 112. When the restorative abutment portion 126 is completely seated on to the central mobile element 112, there will be a 1.0 mm functional space 148, between the inferior aspect 166 of the restorative abutment portion 126 and the external locking surface 146 of the threaded cannulated housing 136 to permit unabated compression of the abutment 126 under function and distribution of the functional forces to the compressive coil 120 (FIG. 17). FIG. 17 illustrates a side sectional view of a restorative abutment portion attached to the superior threaded portion of the central mobile element, in accordance with an embodiment of the present disclosure.

A Step 214 includes positioning the compressive ring 134 on external locking surface 146 of the threaded cannulated housing 136. The compressive ring 134 is positioned prior to the placement of the screw retained dental prosthesis 150. The compressive ring 134 is stretched taught over the restorative abutment portion 126 and advanced inferiorly until it intimately contacts the external locking surface 146 of the threaded cannulated housing 136 and the inferior aspect 166, of the restorative abutment portion 126. This positioning of the compressive ring 134 protects the functional space 148 and force distribution abutment components from moisture contamination and laterally supports the abutment componentry under function A final Step 216 comprises securely seating the dental prosthesis 150 on the restorative abutment portion 126. FIG. 18 illustrates a side sectional view of an exemplary screw rotatably engaging a cavity in the dental prosthesis connecting the prosthesis to the restorative abutment portion and the restorative collar of the dental implant, in accordance with an embodiment of the present disclosure. As shown in FIG. 18, a screw may advance and secure the dental prosthesis 150 thereto. The screw retained dental prosthesis 150 will contact the compressive ring 134, which will provide further force distribution along the collar 110 of the dental implant when functional forces are applied to the assembly 100. From this secure position, the aforementioned micro-motion mechanism is functionality operable.

Since many modifications, variations, and changes in detail can be made to the described preferred embodiments of the disclosure, it is intended that all matters in the foregoing description and shown in the accompanying drawings be interpreted as illustrative and not in a limiting sense. Thus, the scope of the disclosure should be determined by the appended claims and their legal equivalence

What I claim is:

1. A dental implant abutment assembly for uniformly distributing and dissipating occlusal forces, the assembly comprising:
    a dental implant defined by an implant body comprising an external threaded surface and an internal threaded bore, a collar, and a restorative platform;
    a central mobile element defined by a threaded superior portion separated by a shoulder portion from an inferior portion;
    a compressive coil configured to wrap around the length of the inferior portion of the central mobile element, the compressive coil extending between the shoulder portion and the inferior portion of the central mobile element; wherein the compressive coil at least partially supports vertical displacement of the central mobile element for uniformly distributing occlusal forces;
    a threaded cannulated housing defined by a hollow chamber, an inner housing channel, an outer housing threaded surface, a terminal end, and a locking end, the locking end having an inner ridge and an external locking surface, wherein the inner housing channel is configured to enable passage of the threaded superior portion of the central mobile element so that a space forms between the threaded superior portion of the central mobile element and the external locking surface of the cannulated housing, and the inner ridge of the locking end engages the dental implant collar, and wherein the outer housing threaded surface is disposed to rotatably secure with the internal threaded bore of the dental implant body;
    a compressive ring having a central hole, wherein the threaded superior portion of the central mobile element passes through the central hole of the compressive ring, so that the compressive ring positions on the restorative platform of the collar of the dental implant, and occupies the space between the threaded superior portion of the central mobile element and the external locking surface of the housing; and
    a restorative abutment portion defined by an inferior aspect having a threaded cavity and a superior aspect having a threaded central bore, the inferior aspect of the restorative abutment portion is disposed to engage the compressive ring and the threaded superior portion of the central mobile element is configured to pass through the threaded cavity of the inferior aspect of the restorative abutment portion, so that the compressive ring is operatively arranged to dampen occlusal forces on the restorative abutment portion.

2. The assembly of claim 1, further including a dental prosthesis, the dental prosthesis defined by a prosthesis cavity, a restorative margin, and a crown wherein the restorative margin is disposed to engage the restorative platform of the collar of the dental implant.

3. The assembly of claim 2, wherein the dental prosthesis further comprises a screw, the screw configured mate with the threaded central bore of the restorative abutment portion to connect the dental prosthesis to the restorative abutment portion.

4. The assembly of claim 3, wherein the restorative abutment portion is configured to attach the central mobile element to the dental prosthesis and wherein the superior aspect of the restorative abutment portion has a generally the same diameter relative to the inferior aspect.

5. The assembly of claim 2, wherein the restorative abutment portion is configured to attach the central mobile element to the dental prosthesis and wherein the superior aspect of the restorative abutment portion has a diameter relative to the inferior aspect of the restorative abutment portion.

6. The assembly of claim 1, wherein the central mobile element is generally cylindrical shaped.

7. The assembly of claim 1, wherein the inferior portion of the central mobile element is wider than the threaded superior portion.

8. The assembly of claim 1, wherein the internal threaded bore of the implant body terminates at a bore base.

9. The assembly of claim 1, wherein the terminus of the inferior portion of the central mobile element is disposed about 1 millimeter from the bottom of the treaded cannulated housing's inner housing channel terminus.

10. The assembly of claim 1, wherein the inner housing channel of the threaded cannulated housing is tapered, the tapered configuration arranged to restrict movement of the central mobile element and the compressive coil in the hollow chamber of the threaded cannulated housing.

11. The assembly of claim 1, wherein the external locking surface of the housing has three depressions.

12. The assembly of claim 1, wherein the threaded cavity of the inferior aspect of the restorative abutment portion is threaded and disposed to threadably engage the threaded superior portion of the central mobile element.

13. The assembly of claim 11, wherein the three depressions of the external locking surface are configured to engage a torque tool for rotatably engaging the threaded cannulated housing with the internal threaded bore of the implant body.

14. The assembly of claim 1, wherein the compressive ring is dimensioned in a range of 1.5 millimeters to 2.0 millimeters in height, and 1.0 millimeter to 1.5 millimeters in thickness.

15. The assembly of claim 1, wherein the compressive ring compresses about 0.1 to 0.2 millimeters under functional forces.

16. The assembly of claim 1, wherein the compressive ring's positioning about the space between the restorative abutment portion and the external locking surface of the threaded cannulated housing helps restrict moisture in the space between the threaded superior portion of the central mobile element and the external locking surface of the threaded cannulated housing.

17. The assembly of claim 1, wherein the compressive coil is configured to compress about 0.1mm to 0.2mm under functional forces.

18. The assembly of claim 1, wherein the coil is fabricated from a biologically compatible, nonionizing material.

19. A dental implant abutment assembly for uniformly distributing occlusal forces, the assembly comprising:
  a dental implant, the dental implant defined by an implant body, a collar, restorative platform, an external threaded surface, and an internal threaded bore;
  a central mobile element, the central mobile element defined by a threaded superior portion, a shoulder portion, and an inferior portion;
  a compressive coil, the coil configured to wrap around the inferior portion of the central mobile element, the compressive coil extending between the shoulder portion and the inferior portion of the central mobile element, wherein the coil at least partially supports vertical displacement of the central mobile element under function for uniformly distributing occlusal forces;
  a threaded cannulated housing, the housing defined by an inner housing channel, an outer housing threaded surface, a terminal end, and a locking end, the locking end having an inner ridge and an external locking surface, wherein the inner housing channel is configured to enable passage of the central mobile element; and wherein a space forms between the threaded superior portion of the central mobile element and the external locking surface of the housing; and wherein the inner ridge of the locking end engages the implant collar, wherein the outer housing threaded surface is disposed to pass through the internal threaded bore of the implant body;
  a compressive ring, the compressive ring defined by a central hole and a resilient composition, wherein the threaded superior portion of the central mobile element passes through the central hole of the compressive ring, wherein the compressive ring positions on the restorative platform of the collar of the dental implant, wherein the compressive ring substantially occupies the space formed between the threaded superior portion of the central mobile element and the external locking surface of the threaded cannulated housing;
  a restorative abutment portion, the restorative abutment portion defined by an inferior aspect with a central threaded area and a superior aspect having a central threaded area, the inferior aspect of the restorative abutment portion disposed to engage the compressive ring, wherein the threaded superior portion of the central mobile element is configured to pass through the inferior aspect of the restorative abutment portion, and wherein the compressive ring helps dampen occlusal forces on the restorative abutment portion; and
  a dental prosthesis defined by a prosthesis cavity, a restorative margin disposed to engage the restorative platform of the dental implant collar, and a crown with a functional occlusal surface.

20. A method for uniformly distributing occlusal forces with the dental implant abutment assembly of claim 1, the method comprising:
  placing the central mobile element into the compressive coil;
  inserting the central mobile element and the compressive coil into the hollow chamber of the threaded cannulated housing;

advancing the central mobile element and the compressive coil superiorly through the inner housing channel of the threaded cannulated housing until the shoulder portion of the central mobile element contacts the inner ridge on the locking end of the housing;

advancing the threaded cannulated housing, the central mobile element, and the compressive coil into the internal threaded bore of the implant body;

seating the threaded cannulated housing, the central mobile element, and the compressive coil unit with a torque tool;

seating the restorative abutment portion on the threaded superior portion of the central mobile element to depress the restorative abutment portion with the support of the compressive ring;

positioning the compressive ring on the locking end of the threaded cannulated housing; and securely seating a dental prosthesis on the restorative abutment portion of a force distribution abutment assembly.

* * * * *